United States Patent [19]

Woodhams et al.

[11] Patent Number: 5,866,425

[45] Date of Patent: Feb. 2, 1999

[54] CALIBRATOR FOR PROTHROMBIN TIME (PT) ASSAYS

[75] Inventors: Barry J. Woodhams; Michael E. Burgess-Wilson, both of Fribourg, Switzerland

[73] Assignee: Dade AG, Duedingen, Switzerland

[21] Appl. No.: 587,170

[22] Filed: Jan. 16, 1996

Related U.S. Application Data

[63] Continuation of Ser. No. 235,016, Apr. 28, 1994, abandoned.

[51] Int. Cl.$^6$ .......................... G01N 33/48; G01N 38/50; C07K 14/745; C12N 9/64
[52] U.S. Cl. ........................... 436/16; 435/212; 435/226; 436/8; 436/15; 436/811
[58] Field of Search ............................. 435/13, 212, 226; 436/8, 15, 16, 811

[56] References Cited

U.S. PATENT DOCUMENTS

| | | | |
|---|---|---|---|
| 4,461,833 | 7/1984 | Gordon | 435/183 |
| 4,721,572 | 1/1988 | Jordan | 210/635 |
| 4,784,944 | 11/1988 | Kolde | 435/13 |
| 4,865,984 | 9/1989 | Nemerson, et al. | 435/288 |
| 5,059,525 | 10/1991 | Baltl | 435/13 |
| 5,110,730 | 5/1992 | Edgington, et al. | 435/69.6 |

FOREIGN PATENT DOCUMENTS

| | | |
|---|---|---|
| 0158254 | 10/1985 | European Pat. Off. . |
| 278776 | 8/1988 | European Pat. Off. . |
| 0464533 | 6/1991 | European Pat. Off. . |
| 9005740 | 5/1990 | WIPO . |

OTHER PUBLICATIONS

Telgt, et al., "Mechanism By Which Recombinant Factor VIIa Shortens the aPIT . . . ", *Thrombosis Research*, 56(5); 603–609 (1989).

Brown, et al., "Development of a Human Recombinant Tissue Factor", *Clinical Chemistry*, 37 (6); 951@199 (1991).

Tejidor, et al., "Use of Synthetic Phospolipids to Prepare Active Recombinant Human Tissue Factor", *AHA Scientific Sessions –Abstract Form*, (1991).

Rehemtulla, et al., "High Level Expression . . . " *Thrombosis and Haemostasis*, 65 (5); 521–527 (1991).

Roy, et al., "Self–association of Tissue factor . . . ", *The Journal of Biological Chemistry*, 266 (8); 4665–4668 (1991).

Ruf, et al., "Phospholipid–independent and –dependant . . . " *The Journal of Biological Chemistry*, 266 (4) 2158–2166 (1991).

Liang, et al., "Production and Characterization . . . ", *Biochemical and Biophysical Research Communications*, 137 (2); 847–854 (1986).

Scarpati, et al., "Human Tissue Factor . . . ", *Biochemistry*, 26 (17); 5234–5238 (1987).

Wang, et al, "Purification and Characterization . . . ", *Biochem. J.*, 276; 63–71 (1991).

Paborsky, et al., "Purification of Recombinant . . . ", *Biochemistry*, 28 (20); 8072–8077 (1989).

Paborsky, et al., "Post–Translational Modifications . . . ", *Thrombosis Research*, 60; 367–376 (1990).

Konigsberg, et al., "Molecular Cloning of the cDNA for Human Tissue Factor", *Cell*, 52; 639–640 (1988).

*Primary Examiner*—Dian C. Jacobson
*Attorney, Agent, or Firm*—Lois K Ruszala; Louise S Pearson

[57] ABSTRACT

This invention pertains to a PT Assay Calibrator and a method of preparing a PT Assay Calibrator including a coagulation factor such as recombinant FVII or recombinant FVIIa that will allow preparation of PT calibration curves with values about 100% and which will give results analogous to those obtained using fresh normal plasma.

10 Claims, 5 Drawing Sheets

CALIBRATOR FOR PROTHROMBIN TIME (PT) ASSAYS

This is a continuation of application Ser. No. 08/235,016, filed on Apr. 28, 1994 now abandoned.

BACKGROUND OF THE INVENTION

1. Field of the Invention

This invention relates to a method of preparing a commercial plasma preparation that will allow preparation of PT calibration curves with values about 100% and which will give results analogous to those obtained using fresh normal pooled plasma.

2. Description of the Related Art

The Prothrombin Time (PT) is used as a screening test for blood coagulation factor deficiencies and for monitoring oral anti-coagulant therapy using, e.g., coumadin. Thromboplastin reagents activate the "extrinsic" pathway of coagulation and are the basis for the PT test. Thromboplastin contains lipidated tissue factor (TF), which is the activator of the extrinsic pathway. This activation centers on Factor VII (FVII) and activated Factor VII (Factor VIIa), the TF-FVII Complex activates Factor X, which with Factor V activates Factor II to produce thrombin, which creates the fibrin clot.

There are several ways of expressing the results of the PT test. One system, the INR system, is recommended by the World Health Organization. However, many countries have not adopted this system for expressing PT results. Moreover, the INR system has only been validated for patients on oral anticoagulant control, but should not be used in expressing results from patients with other disease states, such as liver disease. Another system, commonly used in the United States, expresses the time in seconds for the blood to begin to coagulate. Still another system expresses the results in terms of a percentage PT ("% PT") which is read from a standard calibration (or dilution) curve prepared by diluting fresh normal pool plasma ("FNP") in 0.9% saline. (Other diluents work, but by convention, only saline is used.) The curve allows for the conversion of results from time in seconds to percent of normal activity (% PT). Unfortunately, in order for this system to be used, most laboratories have to prepare their own pool plasma and keep it frozen, usually in liquid nitrogen or frozen at −80° C. Moreover, due to the inherent variation found in different plasma pools, there is no standardization between the plasma pools of different laboratories. Moreover, it has been shown that if a pool of plasma is prepared, the mean % PT value obtained from the pool is different than the mean % PT value obtained from the individual samples that were used to make the pool. It has also been shown that the collection of bulk collections of blood, as would be required to commercially prepare a lyophilized standard, causes a reduction in the measured % PT when compared with blood collected by venipuncture. See Important Differences Encountered in the Normal Plasma Pools used for the Control of Oral Anticoagulation. M. Burgess-Wilson, R. Burri and B. Woodhams, Thromb. Haemost. 69 Abstract 2081 (1993). Moreover, FNP cannot be sold until lyophilized. Lyophilization results in a plasma which, when reconstituted, has a % PT value lower than that found in a normal hospital pool of plasma. This reconstituted FNP is then used to prepare the standard curve. The dilutions usually used for the standard calibration curve are undiluted, 1:1, 1:2 and 1:4. Where reconstituted FNP is used, the undiluted sample is assigned a value of 100% PT. A PT assay is performed and the results (in seconds) are plotted on hyperbolic or reciprocal graph paper against the dilution (in %). See FIG. 1. Patient samples are tested undiluted and then read from this standard curve. However, using reconstituted FNP as a calibrator means that values for normal samples are above the top calibration point of the standard curve made using the reconstituted FNP. (By definition, 50% of all normal values would be above the top point of the standard curve.)

The % PT curve is not a straight line. Although a polynomial plot gives the most realistic curve through the data, many laboratories and users do not have the computer software required for such a procedure. Therefore, a linear curve through the points is commonly used. To make the results more accurate around the 100% region of the curve, the line is forced through the 100% point. One type of assay machine, the Medical Laboratory Automation ("MLA") Electra automated coagulometers, does not calculate % PT outside of certain ranges (above about 125% PT and below about 12% PT).

The recommended method of calculating % PT varies between the instrument manufacturers. There is no universally used standard procedure. Some instrument manufacturers, such as MLA, recommend forcing a straight line through 100%. Others recommend polynomial or non-forced straight lines. This introduces variability into the procedure, especially if the calibration plasma has a value of % PT much lower than 100%. See FIG. 2. In the examples that follow, the method of calculating the % PT was to use a forced linear curve through the 100% point using the SigmaPlot transformation.

SUMMARY OF THE PRESENT INVENTION

This invention relates to a method for preparing a commercial plasma preparation that will allow calibration curves to be prepared that will have % PT values of about 100% and will give results analogous to those obtained with FNP. In summary, the invention involves the addition of recombinant human FVII or FVIIa (or any other source of FVII, provided it is of high enough purity and behaves in a similar fashion to human FVII) to normal human citrated plasma to give the required PT %. For an article discussing the purification of recombinant human Factor VII, please see Kemball—Cook, Mcvey, Garner, Martin, O'Brien and Tuddenham, *Stable High Level Expression of Recombinant Human Factor VII In Mammalian Cell Culture,* Thromb. Haemostatis 69 (6) 1993, Abstract 253. The resulting plasma is lyophilized and calibrated. It is expected that the addition of other recombinant factors such as rFVIII, rFV or rFXI could be made to a plasma that would also act as a calibrator for other coagulation assays, e.g. FVIII, FV, FXI, derived fibrinogen, FIX, FII, FX, Protein-C, Protein-S, and APTT (clotting and chromogenic) assays. For example, rFV is obtained from available sources and can be added to the plasma such that a level of about 100% rFV is achieved.

The composition for calibration of a PT assay of the present invention (hereinafter 'Calibrator' can be used with thromboplastin reagents such as THROMBOPLASTIN IS lyopholized acetone dehydrated rabbit brain thromboplastin, calcium ions, buffers and stabilizers, hereinafter THROMBOPLASTIN IS, THROMBOPLASTIN C reagent, lyophilized acetone-dehydrated rabbit rain thromboplasint, calcium ions, stabilizers and preservatives, hereinafter THROMBOPLASTIN C reagent, and THROMBOPLASTIN C+ reagent, lyophilized acetone-dehydrated rabbit brain thromboplastin, calcium, buffer, antimicrobial and stabilizers, hereinafter THROMBOPLASTIN C+ reagent. Particularly, the Calibrator of the present invention is designed for use with a recombinant tissue factor PT reagent such as Baxter Diagnostics Inc.'s Dade INNOVIN™ Reagent lyophilized recombinant human tissue factor and phospholipids (thromboplastin), calcium ions, buffers and stabilizers, hereinafter "INNOVIN reagent" and Ortho Diagnostics Systems Ortho® RECOMBOPLASTIN ™ which are used as reagents in the PT determinations and PT-based assays. Recombinant tissue factor reagents, and in particular, INNOVIN™ reagent, was found to have increased sensitivity, when compared to other reagents used in PT determination and PT-based assays, to various factor deficiencies and oral anticoagulant-treated patient samples. The increased sensitivity of such reagents is such that they differentiate much more between FNP collected by syringe or by blood bag than traditional thromboplastins (prepared from animal or human tissue extracts). A calibration plasma should be collected in a fashion similar to clinical samples, i.e., syringe drawn. However, until the Calibrator of the present invention, commercial preparations of a calibration plasma with a PT of 100% were difficult, if not impossible, to prepare. Lyophilized normal plasma has a % PT of 85% or less when measured with INNOVIN™ reagent. The use of a plasma sample with such a low % PT value makes calculations of the % PT value of normal samples difficult and introduces a large amount of variation according to the method used to calculate the % PT, as explained further below. As shown in FIG. 2, the boxed area shows the two curves which can be drawn (polynomial and extrapolated). The enlarged boxed area shown in FIG. 3 demonstrates that the two curves will give very different results as they diverge. The divergence increases above the top calibration point. If the top calibration point is at 85%, then the calibration of normal results (130–70% PT) will be more strongly influenced by the choice of curve as the 85–100% PT part of the curve will have to be extrapolated. The use of the calibrator of the present invention will keep the % PT close to 100% and avoid using the diverging areas of the curves. The resulting calibrated plasma preparation can be used on the MLA Electra, KC, and ACL range of instruments.

DETAILED DESCRIPTION OF THE DRAWINGS

FIG. 4 depicts the effect of the addition of rFVIIa in different concentrations on PT Clotting Time in seconds from the data in Table 1a.

DETAILED DESCRIPTION OF THE INVENTION

Figure 1:
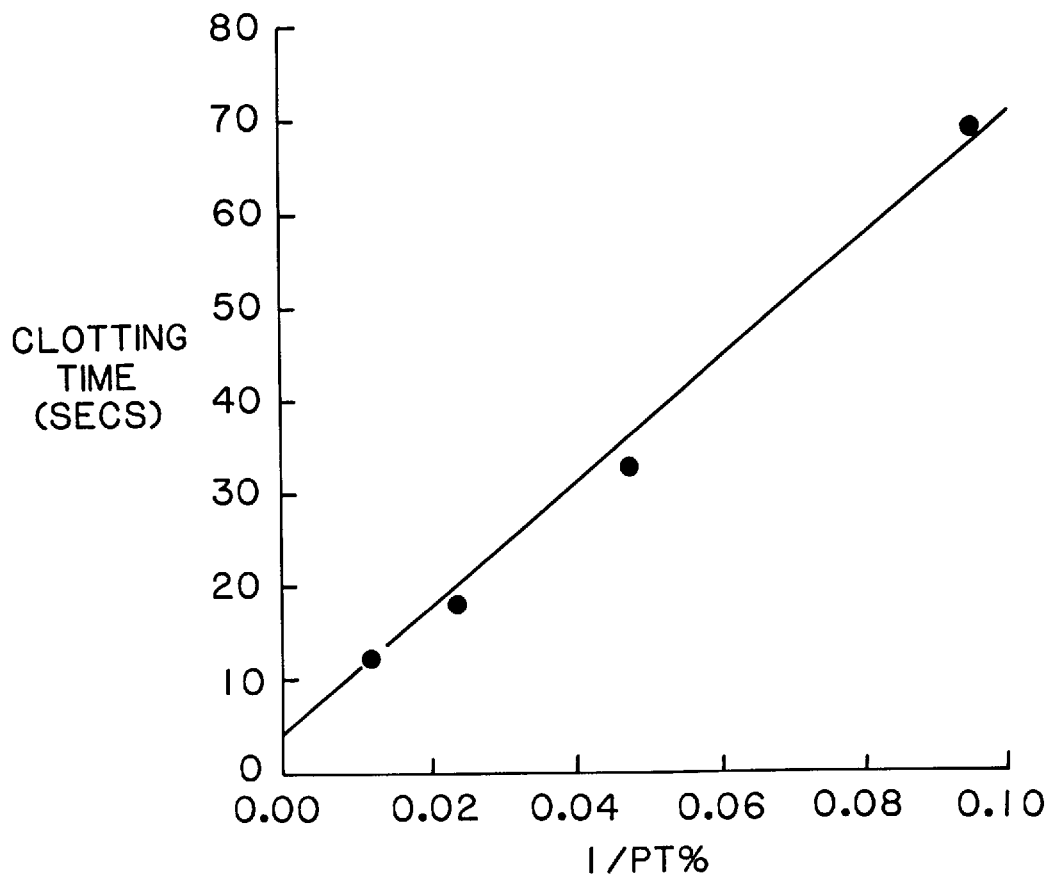
FIG. 1 depicts a calibration curve of clotting time (in seconds) vs. 1/PT % for dilutions of FNP in saline.
Figure 2:
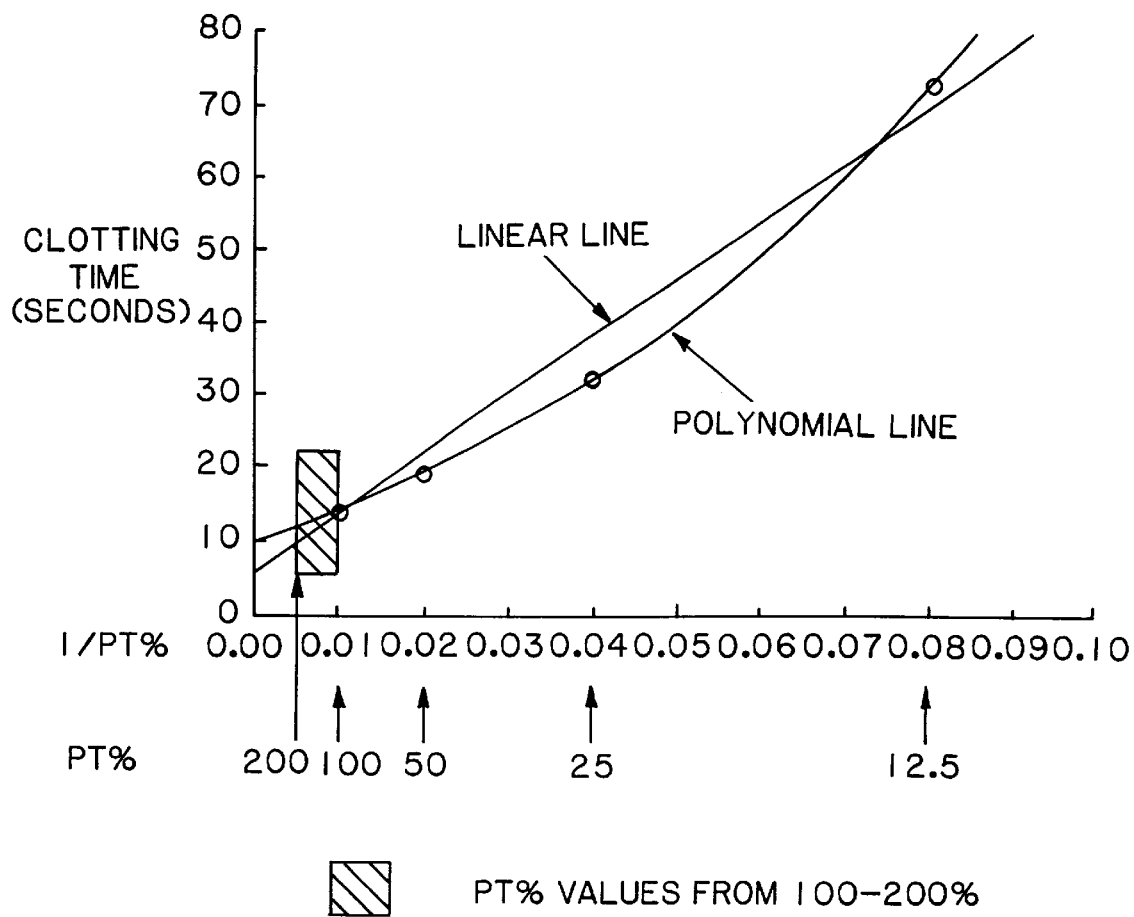
FIG. 2 depicts the problem posed by calculating % PT using PT dilution curves when the clotting time of the test plasma is shorter than that of the calibration plasma.
Figure 3:
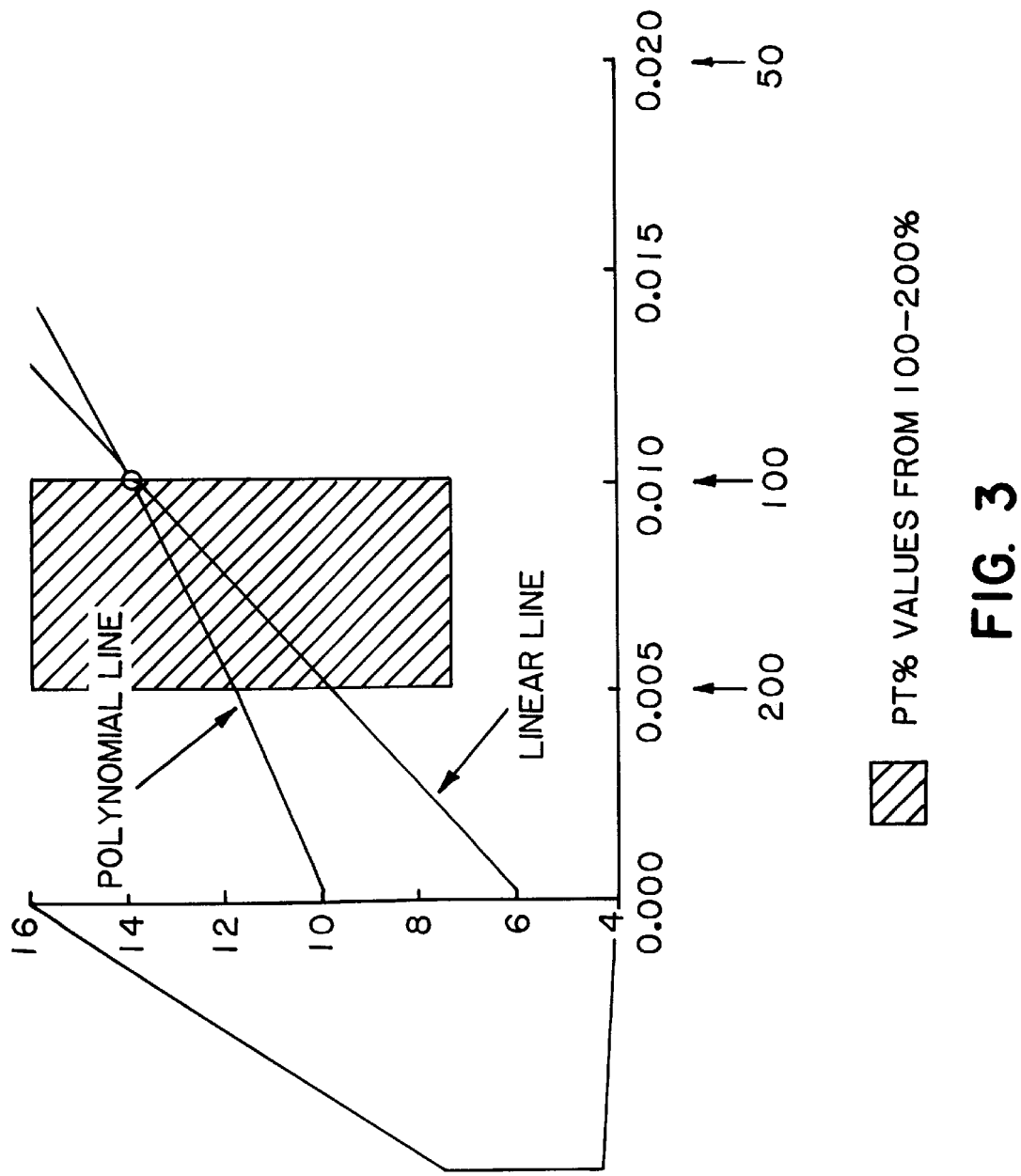
FIG. 3 depicts an enlarged portion of FIG. 2.
Figure 4:
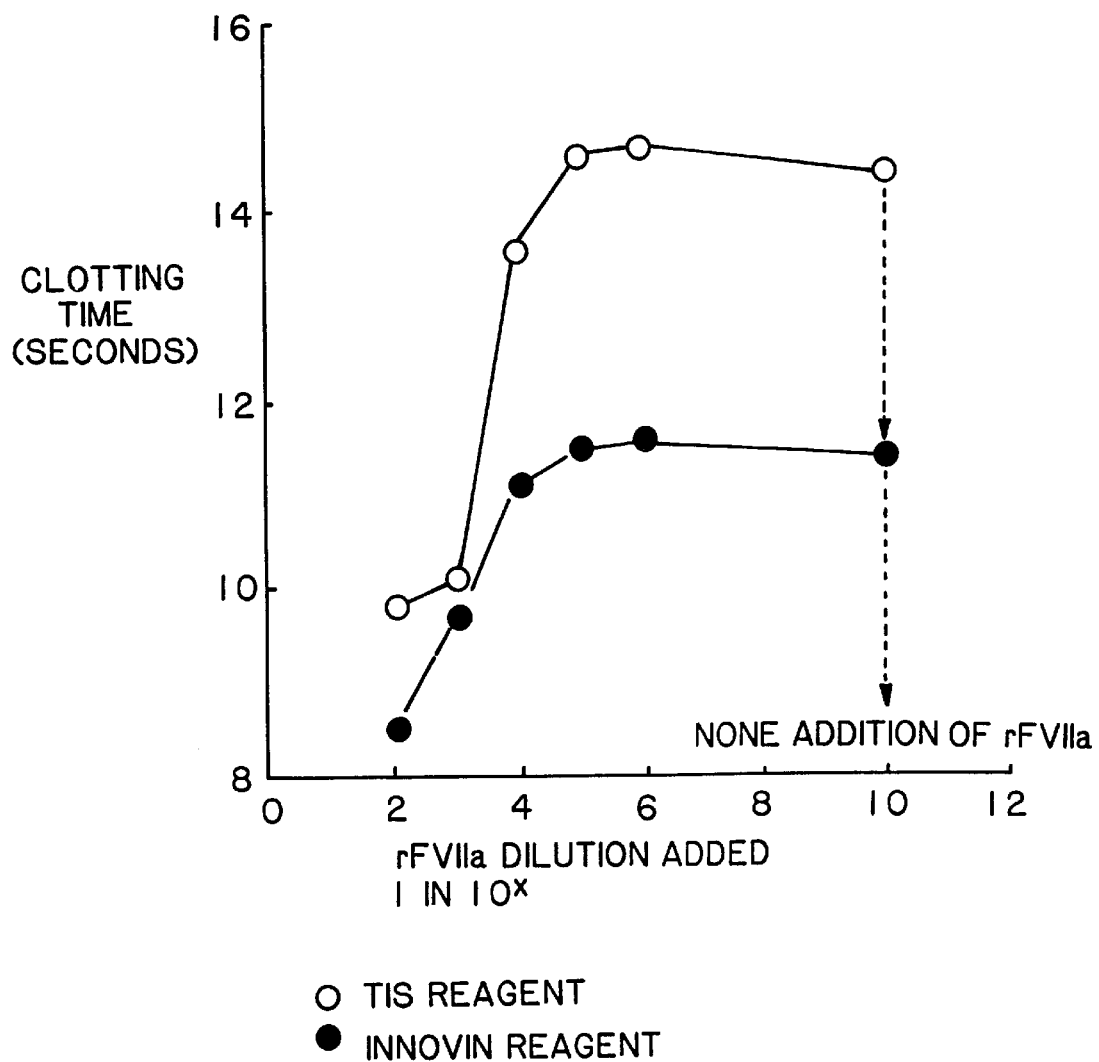

Recombinant FVIIa did raise the % PT of the plasma pool. Recombinant FVII also raised the % PT. The amount of recombinant material needed to be added to a large pool of plasma to produce a % PT of about 100% was determined.

The FVII levels achieved (as measured using the one stage clotting assay) did not usually parallel the rise in PT %. Two lots of rFVII showed quite different relationships between PT % and FVII level rise. The difference was thought to be due to "contamination" of the rFVII with the more active rFVIIa. As described later herein, the rFVIIa material did not have this problem. Without limiting the scope of the invention, it is believed that rFVIIa is preferable as a calibrator because the "contamination" factor is not present.

Either rFVII or rFVIIa was added to a pool of HEPES buffered citrated plasma. While HEPES buffer was chosen for these examples because it lyophilizes well, it is believed that most buffers which work in the physiological pH range could be used, except for phosphate type buffers. Examples of buffers which should work include Good's Buffers: PIPES, ACES, BES, MOPS, TES, and TRICINE. The resulting plasma plus recombinant material was tested for PT % prior to lyophilization. Two lots of the plasma plus rFVII had a PT % of about 100% prior to lyophilization. After lyophilization, the PT % was about 85%. The PT % calibration curve from such reconstituted plasma was used to calculate PT % results. Values were very similar to those obtained using a calibration curve from COAG CAL ("CCN") plasma, a lyophilized, intrated normal plasma containing all clotting factors.

Three lots of the calibrator plasma were produced by adding rFVIIa to a pool of HEPES buffered citrated plasma. The accelerated stability studies showed that after 35 days at 37° C. (equivalent to 2 years at 4° C.), the results were similar to those of CCN plasma and suggests they will have a similar stability. In two lots, the PT % was adjusted to approximately 100% before lyophilization. Lyophilization appeared to reduce the PT % to between 90–95%. The pre-lyophilization target for the third lot was changed to between 105% and 108%, inclusive. Post-lyophilization, the third lot had a PT % of about 100%. The reconstituted third lot was stable for 8 hours at 4° C. and room temperature. The PT % calibration curves from such lot were stable for 30 minutes.

As more fully explained in the examples, one or more of the following reagents were used in the examples that follow. (These examples are intended for purposes of illustration of the invention, not for limitation of the invention. For instance, the addition of HEPES is referred to as "dropwise" in an example. The invention obviously is not limited to use of the HEPES buffer or its dropwise addition.)

| Recombinant material: | | | |
|---|---|---|---|
| Material | Lot No. | Concentration | Source |
| rFVIIa | 29491 | 1 mg/ml (Novo) | Düdingen |
| rFVIIa | 8293 | 1.2 mg/ml (Novo) | Harrow |
| rFVII | 28193 | 30–40 U/ml | Harrow |
| rFVII | 9393 | 24 U/ml | Harrow |
| rFVII | 10393 | 15 U/ml | Harrow |
| rFVIIa | 21593 | 2500 U/ml | Harrow |

Harrow refers to the Haemostasis Research Group, Clinical Research Centre, Watford Road, Harrow, Middlesex, England.

Other reagents:
TIS THROMBOPLASTIN IS lots TPS—46 and 59 (Baxter's dried rabbit brain with calcium PT assay reagent)
INNOVIN™ INNOVIN™ reagent lots TFS—12, 13, 14 and 24
Saline NaCl (0.9%) lots H1-75
Owrens Buffer Owrens Buffer lots 550.029, 550.030 and 550.032
Factor VII Immuno Absorbed Plasma ("IAP") Factor VII IAP lots IAP7-25A and 26A
FVII(a) -Tris Buffer Tris Buffer pH 7.4 lots H1-85 Buffer used to dilute rFVII (Although TRIS buffer is used in these examples, it is believed that any buffer of the same pH can be used.) 0.05M Tris (hydroxymethyl)-aminomethane 0.15M NaCl
Several lots of CCN plasma, a lyophilized normal plasma containing all clotting factors, were tested for PT % using THROMBOPLASTIN IS and INNOVIN™ reagents. They were also tested for the FVII % level. The results are tabulated below. The five lots of CCN plasma were combined to make FNP 870.003.

| CCN lot No. | PT % TIS | PT % Innovin ™ | FVII % level |
|---|---|---|---|
| 540.042 | 92 | — | 98 |
| 540.049 | 91 | 85 | 105 |
| 540.050 | 100 | 85 | — |
| 540.053 | 97 | 85 | 97 |
| 540.054 | — | — | — |
| FNP 870.003 | 100 | 100 | 100 |

Machines and software:
MLA Electra 1000C: No 572—Software Version 3 Rev. E
MLA Electra 900C: No 1753—Software Version 4 Rev. 1
MLA Electra 1000C: Software Version 5.0: Munchen Methods:
Prothrombin Time (PT)
The PT testing assays were performed as per the Box Inserts for THROMBOPLASTIN IS and INNOVIN™ reagents, and the MLA Electra 900C or 1000C operating manuals.

Factor VII assay
Factor VII assays were performed as per the Box Insert of the FVII IAP and the MLA Electra 900C or 1000C operating manuals. The dilutions of the plasma or concentrate were selected so that the clotting times obtained were within the range obtained using the calibration curve dilutions. In general, the 1 in 10 dilution was assigned as 100% Factor VII.

EXAMPLE I

Recombinant FVIIa lot 29491 was diluted in Owrens Buffer $1/10^2$, $1/10^3$, $1/10^4$, $1/10^5$, $1/10^6$, and $1/10^7$. Five 500 ul aliquots of FNP 870.003 were prepared. To each of the aliquots of FNP 870.003 were added one 20 ul aliquot of one rFVIIa dilution. The PT % of the resulting plasmas were tested using the MLA Electra 900C.

Figure 5:
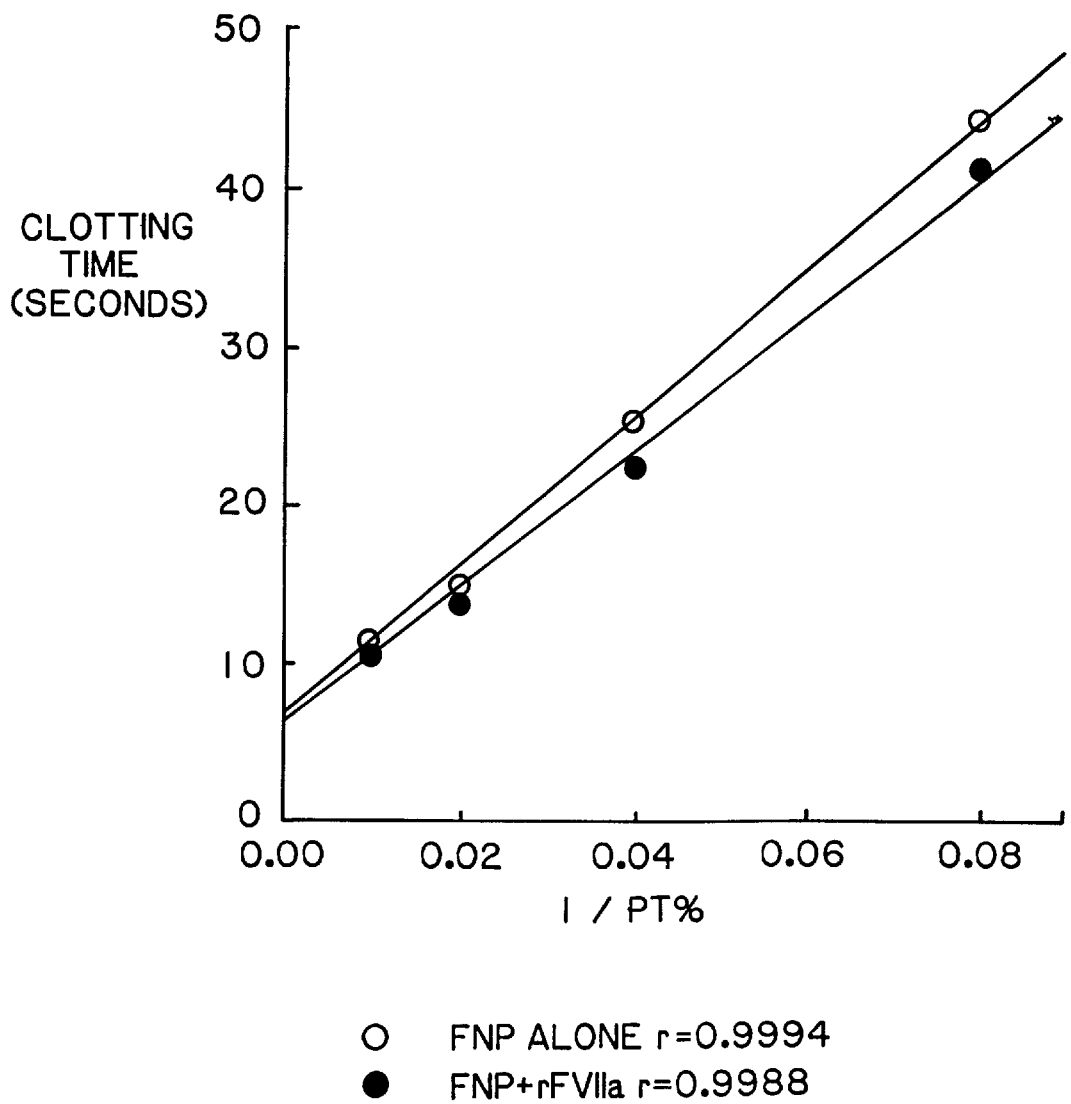
FIG. 5 depicts the PT calibration curves of FNP alone and FNP with the addition of rFVIIa (1/10$^3$ dilution), from the data in Table 1b.

When measured using THROMBOPLASTIN IS and INNOVIN™ reagents, it was possible to reduce the PT clotting time of FNP, thus increasing the % PT. (See Table 1a). Using the $1/10^4$ dilution of the rFVIIa, the Factor VII % level in the FNP was raised by 13–20%. The calibration curves (Clotting Time, in seconds, vs. 1/PT %) of FNP and FNP plus rFVIIa were nearly parallel, indicating that the modified plasma (FNP plus rFVIIa) can be used as a calibrator. See Table 1b and FIG. 5.

TABLE 1

Effect of different concentrations rFVIIa in FNP on PT
Table 1a: rFVIIa dilutions in FNP

| | PT Clotting Time (seconds) | |
|---|---|---|
| Dilution added In FNP | THROMBOPLASTIN IS | INNOVIN ™ |
| None | 14.4 | 11.4 |
| 1/100 | 9.8 | 8.5 |
| 1/1000 | 10.1 | 9.7 |
| 1/10,000 | 13.6 | 11.1 |
| 1/100,000 | 14.6 | 11.5 |
| 1/1,000,000 | 14.7 | 11.6 |
| Buffer | 14.8 | 11.5 |

TABLE 1b:

Data for rFVIIa 10 3 dilution in FNP, calibration curve, compared with data for FNP curve

| | PT Clotting Time (seconds) | | | |
|---|---|---|---|---|
| | FNP | | FNP + rFVIIa 10 3 | |
| Dilution | TIS | INNOVIN ™ | TIS | INNOVIN ™ |
| Neat | 14.5 | 11.5 | 12.6 | 10.5 |
| 1 in 2 | 20.2 | 15.0 | 17.4 | 13.7 |
| 1 in 4 | 32.0 | 25.5 | 27.9 | 22.4. |
| 1 in 8 | 56.1 | 44.3 | 51.7 | 41.2 |

EXAMPLE II

Recombinant FVIIa Lot 8293 was diluted in CCN plasma lot 049 by adding 50 ul of concentrated rFVIIa to 5 ml of CCN plasma, resulting in a 1 in 100 dilution. Then a range of 1 in 10 dilutions were produced by adding 500 ul of the resulting plasma to 4.5 ml of the CCN plasma. Three further dilutions were made, resulting in $1/10^3$, $1/10^4$ and $1/10^5$ dilutions. The CCN plasma lots and the four dilutions were tested using TIS and INNOVIN™ reagents. The results are set forth below:

TABLE 2

Addition of rFVIIa to CoagCal N plasma

| | THROMBOPLASTIN IS | | | | INNOVIN | | | |
|---|---|---|---|---|---|---|---|---|
| Sample | Neat | 1 in 2 | 1 in 4 | 1 in 8 | Neat | 1 in 2 | 1 in 4 | 1 in 8 |
| CCN 042 | 15.1 | 22.5 | 40.2 | 73.4 | 11.9 | 16.3 | 27.3 | 53.1 |
| CCN 049 | 15.0 | 22.6 | 37.6 | 75.6 | 12.0 | 16.0 | 27.5 | 51.1 |
| 1/100,000 | 12.2 | 17.3 | 29.7 | 57.6 | 10.3 | 13.5 | 21.8 | 40.6 |
| 1/10,000 | 10.7 | 15.4 | 25.6 | 50 | 9.7 | 12.2 | 19.1 | 35.6 |
| 1/1,000 | 9.8 | 13.6 | 22.0 | 41.5 | 8.9 | 11.0 | 16.3 | 28.5 |
| 10 2 | 9.5 | 13.2 | 21.9 | 42.6 | — | 10.9 | 16.3 | — |

CCN plasma, like FNP, experienced a reduction in PT, thus increasing the % PT by the addition of rFVIIa.

EXAMPLE III

Testing was done on rFVII material. Reagents included FNP 870.003 and CCN plasma lot 042. Testing was performed on the MLA Electra 1000C.

Different volumes of the three lots of rFVII were added to CCN plasma lot 042. Because the rFVII preparation had lower FVII activity than the rFVIIa preparation, instead of diluting the FVII preparation and adding the dilution to the plasma as in Example I, a different method was used as described below. This was done by reducing the amount of distilled water added to reconstitute the CCN plasma by the volume of rFVII added. For example, when 100 ul rFVII was added, the vial of CCN plasma was reconstituted with only 900 ul of distilled water.

The % PT and FVII % of the reconstituted CCN plasma lot 042 samples were calculated using the FNP calibration curve assigned as 100% PT activity. The mean % PT for all calibration curve dilutions was used. All lots of rFVII raised the % PT and the Factor VII % levels. The effect on the % PT was not proportional to the rise in FVII activity. It was thought that the lots of "rFVII" may have activated rFVII present in variable amounts which led to a variable effect on the % PT which was not related to the assigned Factor VII level. Because of the variability in rFVII, the use of rFVIIa would be preferable as it would be a more consistent reagent.

TABLE 3

Addition of rFVII to CoagCal N plasma

| Sample | | PT % | | Factor VII % | |
| --- | --- | --- | --- | --- | --- |
| | | THROMBOPLASTIN IS | INNOVIN ™ | TIS | INNOVIN ™ |
| | FNP | 100 | 100 | — | — |
| | CCN | 90 | 95 | 98 | 98 |
| rFVII | 75 ul | 92 | 98 | 112 | 110 |
| 9393 | 100 ul | 97 | 102 | 118 | 116 |
| | 100 ul | 96 | 100 | 130 | 124 |
| rFVII | 20 ul | 108 | 108 | 116 | 104 |
| 28192 | 30 ul | 108 | 115 | 200 | 202 |
| | 50 ul | 121 | 120 | 284 | 304 |
| rFVII | 150 ul | 94 | 93 | 138 | 116 |
| 10393 | 200 ul | 97 | 94 | 134 | 118 |

Factor VII calculated using CCN plasma as calibrator PT % calculated assuming FNP=100%

EXAMPLE IV

The method of measuring the Factor VII in the concentrate was investigated and the relationship of the Factor VII levels and PT % in CCN plasma with different amounts of rFVIIa added was examined. Reagents included rFVIIa lot 21593, CCN plasma lots 042 and 049 and IAP7-26A.

Testing was performed on the MLA Electra 1000C. The Factor VII level of the rFVIIa preparation was measured in two ways, by adding the preparation to CCN plasma and assaying dilutions of 1/100 to 1/1000 in Owrens buffer.

A primary dilution of rFVIIa in CCN plasma was made (CCN plasma 5ml plus 20 ul rFVIIa), also referred to as "plasma+rFVIIa". Then the following dilutions were made from the plasma+rFVIIa and CCN plasma. See Table 4. The 10 ul dilution of Table 4, marked with the "*", is the same 10 ul dilution used in Table 5.

TABLE 4

Dilutions of rFVIIa in CoagCal N plasma

| Amount of rFVIIa in 5 ml CCN | 10 ul* | 5 ul | 4 ul | 3 ul | 2 ul | 1 ul | 0 ul |
| --- | --- | --- | --- | --- | --- | --- | --- |
| Primary dilution | 1 ml | 0.5 ml | 0.4 ml | 0.3 ml | 0.2 ml | 0.1 ml | 0 ml |
| CCN | 1 ml | 1.5 ml | 1.6 ml | 1.7 ml | 1.8 ml | 1.9 ml | 2.0 ml |

TABLE 5

Further dilutions of rFVIIa

| Amount of rFVIIa in 5 ml CCN | 2 ul | 1 ul | 0.5 ml | 0.25 ul | 0.125 ul | 0 ul |
| --- | --- | --- | --- | --- | --- | --- |
| 10 ul dilution* | 1 ml | 0 ml | 0 ml | 0 ml | 0 ml | 0 ml |
| CCN | 4 ml | 1 ml | 1 ml | 1 ml | 1 ml | 2 ml |
| Mix + Transfer Previous Dilution | 0 ml | 1 ml | 1 ml | 1 ml | 1 ml | 0 ml |

The results are found in Tables 8 and 9. The following formula was used to calculate the FVII % concentration in U/ml.

$$(FVII \%/100 \times 5) - 5 \times (1000/ul \text{ of rFVIIa added}) = FVII \text{ of the concentrate (U/ml)}$$

| FVII %/100 | 100% FVII = 1 U/ml |
| --- | --- |
| ×5 | 5 ml of plasma |
| −5 | 5 U/ml of FVII in this 5 ml of normal plasma |
| 1000/ul rFVIIa added | Volume of rFVIIa compared to 1000 ul added |

Results were calculated for plasma+rFVIIa using the formula set forth above.

TABLE 6

Calculation of FVII levels - rFVIIa added to plasma

| Amount rFVIIa added | rFVIIa FVII % | FVII (U/ml) |
| --- | --- | --- |
| 5 ul | 253 | 1532 |
| 4 ul | 246 | 1830 |
| 3 ul | 224 | 2070 |
| 2 ul | 197 | 2437 |
| 1 ul | 167 | 3345 |
| mean | 218 | 2243 |

Table 6 shows that the concentrate FVII level was 2243 U/ml when rFVII was added to plasma.

TABLE 7

Calculation of FVII levels - dilutions of rFVIIa in buffer

| Dilution | FVII % | FVII % effective | FVII (U/ml) |
|---|---|---|---|
| 1/1000 | 441 | 44100 | |
| 1/2000 | 292 | 58400 | |
| 1/4000 | 190 | 76000 | |
| mean | | 59500 | 595 |
| 1/10000 | 93 | 93000 | |
| 1/20000 | 51 | 102000 | |
| 1/40000 | 29 | 116000 | |
| mean | | 103667 | 1037 |

Table 7 shows that the concentrate FVII level was between about 600 and 1000 U/ml when rFVII diluted in buffer was tested.

When measuring rFVIIa in plasma, the result obtained (2243 U/ml) was similar to the quoted concentrated from Harrow (2500 U/ml). Estimates using diluted concentrate were lower (600–1000 U/ml) and we concluded that this method is not useful.

A progressive rise occurs in % PT and FVII levels with increasing the addition volume of rFVIIa to plasma (Tables 8 and 9). As seen from the data in Table 9, there was a relationship between the rise in Factor VII level and the rise in PT %, r=0.9661.

TABLE 8

Effect of rFVIIa on Prothrombin Time Lot rFVIIa 21593

| Amount rFVIIa | INNOVIN ™ PT % Calibrator curve dilutions | | | | Test |
|---|---|---|---|---|---|
| Added | Neat | 1 in 2 | 1 in 4 | 1 in 8 | Mode |
| 10 ul | 10.1 | 14.8 | 24.2 | 50.4 | 10.5 |
| 5 ul | 10.4 | 15.3 | 25.5 | 49.7 | 10.5 |
| 4 ul | 10.6 | 15.7 | 26.7 | 53.8 | 10.9 |
| 3 ul | 10.8 | 16.5 | 28.3 | 55.9 | 10.8 |
| 2 ul | 11.1 | 16.4 | 28.2 | 58.5 | 11.3 |
| 1 ul | 11.5 | 17.4 | 30.8 | 60.6 | 11.4 |
| zero | 12.4 | 19.2 | 34.2 | 67.2 | 12.5 |
| 2 ul | 10.8 | 15.8 | 27.4 | 54.6 | 10.9 |
| 1 ul | 11.0 | 16.7 | 29.2 | 61.5 | 11.0 |
| 0.5 ul | 11.3 | 17.2 | 30.8 | 64.0 | 11.4 |
| 0.25 ul | 11.6 | 17.7 | 31.6 | 64.6 | 11.7 |
| 0.125 ul | 11.7 | 18.1 | 32.8 | 66.0 | 11.7 |
| zero | 12.0 | 18.9 | 34.4 | 62.6 | 12.0 |

| Amount rFVIIa | THROMPBOPLASTIN IS PT % Calibrator curve dilutions | | | | Test |
|---|---|---|---|---|---|
| Added | Neat | 1 in 2 | 1 in 4 | 1 in 8 | Mode |
| 10 ul | 11.4 | 17.7 | 30.5 | 62.1 | — |
| 5 ul | 12.0 | 19.0 | 32.0 | 66.9 | — |
| 4 ul | 12.3 | 19.0 | 33.6 | 66.5 | — |
| 3 ul | 12.4 | 19.3 | 33.7 | 71.4 | — |
| 2 ul | 12.8 | 20.4 | 34.4 | 73.0 | — |
| 1 ul | 13.3 | 21.2 | 36.3 | 76.3 | — |
| zero | 15.2 | 24.7 | 41.9 | 85.9 | — |

TABLE 9

Investigation of increasing PT % and FVII % level

| | INNOVIN ™ | | | |
|---|---|---|---|---|
| Amount rFVIIa Added | FVII % Dilution 1 in 10 | PT % | Rise in PT % | Rise in FVII % |
| 10 ul | — | 131 | 33 | — |
| 5 ul | 253 | 131 | 33 | 142 |
| 4 ul | 246 | 123 | 25 | 135 |
| 3 ul | 224 | 125 | 17 | 113 |
| 2 ul | 197 | 115 | 17 | 86 |
| 1 ul | 167 | 114 | 16 | 56 |
| zero | 111 | 98 | 0 | 0 |
| 2 ul | — | 118 | 18 | — |
| 1 ul | — | 116 | 16 | — |
| 0.5 ul | — | 109 | 9 | — |
| 0.25 ul | — | 104 | 4 | — |
| 0.125 ul | — | 104 | 4 | — |
| zero | — | 100 | 0 | — |

| | Thromboplastin IS | | | |
|---|---|---|---|---|
| Amount rFVIIa Added | FVII % Dilution 1 in 10 | PT % | Rise In PT % | Rise In FVII % |
| 10 ul | — | 161 | 61 | — |
| 5 ul | — | 146 | 46 | — |
| 4 ul | — | 140 | 40 | — |
| 3 ul | — | 138 | 38 | — |
| 2 ul | — | 131 | 31 | — |
| 1 ul | — | 123 | 23 | — |
| zero | — | 99.5 | 0 | — |

EXAMPLE V

Stable lyophilized plasma which has had Factor rFVII added to be used as a calibrator in the PT % test was prepared as follows.

Reagents used were rFVII lots 28193 and 9393, plasma as described in Table 11a, and HEPES buffer H1-83.

The volume of rFVII needed was calculated as follows. It was expected that after lyophilization the PT % would be about 85–90%; thus a rise in PT % of 10–15% was required. Preliminary work with lot 28193 suggested that 20–30 ul rFVII per 5 ml of plasma created the desired rise in PT %; 25 ul rFVII per 5 ml of plasma was used. Lot 9393 had a lower Factor VII level and about 400 ul rFVII per 5 ml plasma was needed to raise the PT %.

Ten units of approximately 200 ml each of plasma were selected from each of the plasma bags described in Table 11a. All plasma had been collected into the anticoagulant CPD-A. The plasma was carefully thawed in a large waterbath at 37° C. Bag contents were mixed until all ice had disappeared and the plasma was free from undissolved precipitate. Once thawed, the bags were kept in crushed ice. The entire contents of each bag were pooled and stirred thoroughly while kept cool by crushed ice. Four pools were prepared for lyophilization as described in Table 10.

TABLE 10

Preparation of different plasma pools

| Pool | Volume of plasma | Volume of HEPES | Volume recombinant FVII |
|---|---|---|---|
| Pool P | 100 ml | None | None |
| Pool P1 | 100 ml | 3 ml | None |
| Pool P1 & 28193 | 100 ml | 3 ml | 500 ul of lot 28193 |
| Pool P1 & 9393 | 100 ml | 3 ml | 8 ml of lot 9393 |

HEPES was added dropwise to the stirred plasma. The recombinant FVII was added last and the final mixture stirred thoroughly. The resulting plasmas were pipetted into separate 1.1 ml vials and stored at 4°–8° C. for about 1 hour before lyophilization. After lyophilization, the vials were kept at 4°–8° C. Several vials from each lot were not lyophilized but stored at −70° C. storage. Prior to lyophilization, the different pools of plasma, CCN plasma lot 042 and CCN plasma lot 049, both freshly reconstituted, were tested using the MLA Electra 1000C. Both PT % and FVII % level assays were performed. Plasma samples were tested in the calibration curve mode and in the test mode. The 10 plasmas used to make up Pool P were all normal (see Table 11a). Testing of fresh pools suggest a PT % of approximately 100% in both pools (P1 & 28193, P1 & 9393). The rise in FVII was 140% and 190%, respectively. The conclusion is that the amount of rFVII needed to prepare a control with approximately 100% PT can be predicted. Prior to lyophilization, the addition of HEPES buffer reduced the PT % by about 5%.

After lyophilization, the different pools of plasma, CCN plasma lot 042 and CCN plasma lot 049 were tested using the same instrument and procedure as in their testing before lyophilization. After lyophilization, the pool without HEPES showed a loss of 11% PT whereas the pool with HEPES showed no difference. The two pools with rFVII showed a slight (2%) loss in % PT. No changes were seen in FVII % levels after lyophilization even in the pool without HEPES. (See Tables 12a–12b.)

TABLE 11a

PT Clotting Time of plasmas making up plasma Pool P

| BAG No. | Clotting Time 1020 hrs | 1344 hrs |
|---|---|---|
| 1 | 11.6 | 11.2 |
| 2 | 11.5 | 11.1 |
| 3 | 12.8 | 12.4 |
| 4 | 11.8 | 11.4 |
| 5 | 12.7 | 12.3 |
| 6 | 11.8 | 11.3 |
| 7 | 12.3 | 11.6 |
| 8 | 12.3 | 11.7 |
| 9 | 12.1 | 11.6 |
| 10 | 11.2 | 11.0 |
| Mean | 12.01 | 11.56 |

TABLE 11b

PT Clotting Times before lyophilization
INNOVIN ™ PT Reagent

| Calibrator | Calibration Curve | | | | Test Mode | PT % ** |
|---|---|---|---|---|---|---|
| | Neat | 1 in 2 | 1 in 4 | 1 in 8 | | |
| CCN 049 | 12.2 | 18.0 | 32.7 | 69.0 | 12.14 | 84.2 |
| CCN 042 | 12.2 | 18.3 | 31.9 | 68.3 | 12.16 | 84.0 |
| Pool P | 11.6 | 17.6 | 32 | 66.9 | 11.56 | 91.3 |
| Pool P1 | 12.1 | 18.6 | 32.8 | 66.2 | 11.99 | 86.0 |
| Pool P1 & 28 | 11.1 | 15.7 | 28.4 | 58.1 | 10.95 | 100.1 |
| Pool P1 & 93 | 11.0 | 16.1 | 27.0 | 58.6 | 11.06 | 98.4 |

TABLE 11c

Factor VII assay before lyophilization
INNOVIN ™ PT Reagent

| Cali-brator | Calibration Curve | | | | | Test | FVII % | FVII % |
|---|---|---|---|---|---|---|---|---|
| | 1 in 10 | 1 in 20 | 1 in 40 | 1 in 80 | 1 in 160 | Mode 1 in 10 | 1/10** | 1/20** |
| CCN 042 | 23.1 | 21.4 | 41.2 | 53.6 | 69.7 | 23.2 | 110 | 104 |
| CCN 049 | 23.4 | 31.5 | 42.1 | 54.1 | 70.4 | 23.1 | 111 | 103 |
| Pool P | 24.3 | 32.9 | 43.9 | 57.7 | 74.3 | 23.5 | 107 | 93 |
| Pool P1 | 24.5 | 33.9 | 43.6 | 56.5 | 72.4 | 23.6 | 105 | 86 |
| Pool P1 & 28 | 20.4 | 27.8 | 35.8 | 47.4 | 63.3 | 20.8 | 144 | 141 |
| Pool P1 & 93 | 18.1 | 23.6 | NA | 39.8 | 54.1 | 18.3 | 198 | 210 |

**Calculated with CCN plasma 049 calibration Curve: PT % = 85%, FVII % = 105%

"Test Mode" means that a sample can be tested as a calibrator whether the sample is diluted or just as neat plasma.

TABLE 12a

PT Clotting time after lyophilization
INNOVIN ™ PT Reagent

| INNOVIN ™ Calibration | Calibration Curve | | | | Test Mode | PT % ** |
|---|---|---|---|---|---|---|
| | Neat | 1 in 2 | 1 in 4 | 1 in 8 | | |
| CCN 049 | 12 | 17.5 | 30.8 | 63.1 | 12.15 | 84.1 |
| CCN 042 | 12.2 | 17.8 | 30.9 | 65.7 | 12.05 | 85.3 |
| Pool P | 12.5 | 18.9 | 33.1 | 66.9 | 12.55 | 79.9 |
| Pool P1 | 11.8 | 18.1 | 31 | 65.4 | 11.85 | 87.6 |
| Pool P1 & 28 | 11 | 16.3 | 27.4 | 57.9 | 11.05 | 98.5 |
| Pool P1 & 93 | 11.1 | 15.9 | 26.5 | 54.6 | 11.2 | 96.3 |

TABLE 12b

Factor VII assay after lyophilization

| Calibrator | Calibration Curve | | | | | Test Mode | | FVII % ** |
|---|---|---|---|---|---|---|---|---|
| | 1 in 10 | 1 in 20 | 1 in 40 | 1 in 80 | 1 in 160 | 1 in 10 | 1 in 10 | |
| CCN 049 | 23.1 | 30.2 | 40.9 | 54.2 | 71.7 | 23.5 | 23 | 112 |
| CCN 049 | 23.5 | 31.1 | 41.1 | 53.6 | 71.3 | — | — | — |
| CCN 042 | 23.6 | 31.7 | 42.9 | 56.1 | 72.6 | 23.6 | 23.6 | 105 |
| Pool P | — | — | — | — | — | 23.2 | 24.1 | 100 |
| Pool P1 | — | — | — | — | — | 23.9 | 23 | 112 |

TABLE 12b-continued

Factor VII assay after lyophilization

|  | Calibration Curve | | | | | Test Mode | | |
|---|---|---|---|---|---|---|---|---|
| Calibrator | 1 in 10 | 1 in 20 | 1 in 40 | 1 in 80 | 1 in 160 | 1 in 10 | 1 in 10 | FVII % ** |
| Pool P1 & 28193 | — | — | — | — | — | 20.5 | 20.3 | 153 |
| Pool P1 & 9393 | — | — | — | — | — | 18.2 | 18.1 | 203 |

**Calculated with CCN plasma 049 calibration Curve: PT % = 85%, FVII % = 105%

EXAMPLE VI

Stable, lyophilized plasma to which rFVIIa has been added to be used as a calibrator in the PT % test was prepared as follows.

Reagents used were rFVIIa Lot 21593, Pool 2 (CCN plasma lot 053 just before lyophilization), and TRIS Buffer Lot H1-85. Four hundred milliliters of a plasma pool ready to use (containing HEPES) were used to prepare CCN plasma lot 053.

TABLE 13

Preparation of different plasma pools

| Pool Name | rFVIIa added | Plasma pool 053 | [FVII] added |
|---|---|---|---|
| Pool P2 | None | 100 ml | None |
| Pool P2/20 | 20 ul | 100 ml | 1 ul/5 ml |
| Pool P2/10 | 5 ul | 50 ml | 0.5 ul/5 ml |

| Pool Name | Tris Buffer added | Plasma pool 053 | [Tris B.] added |
|---|---|---|---|
| Pool P2/B | 20 ul | 100 ml | 1 ul/5 ml |

Vials were filled with 1.1 ml pooled plasma and stored at −70° C. for five days and then lyophilized. A certain number of vials were kept at −70° C. and not lyophilized.

Prior to lyophilization, the four pools were tested on the MLA Electra 1000C. After lyophilization, the four pools were tested against the corresponding four frozen pools using the same instrument and procedure as in the testing prior to lyophilization.

The results found in Tables 14 and 15 were calculated using a previous CCN plasma lot 049 calibration curve (Table lib: 12.2, 18.0, 32.7 and 69.0 seconds assigned as 85% PT). The fresh results for two lots (Pool P2/20 and Pool P2/10) are 102% and 98% respectively. After lyophilization, there appears to be a 5–8% drop in the PT %, which did not occur with rFVII. The frozen samples did not show this drop. It appears that in plasmas where rFVIIa is used to increase the PT %, there is a 5–8% loss of PT % during lyophilization. This needs to be compensated for during the manufacturing process.

TABLE 14

Pool P2 fresh before the lyophilization

|  | Calibration Curve | | | | Test | PT % |
|---|---|---|---|---|---|---|
| INNOVIN ™ | Neat | 1 in 2 | 1 in 4 | 1 in 8 | Mode | ** |
| Pool P2 | 12.3 | 17.7 | 30.5 | 60.1 | 12.1 | 84.7 |
| Pool P2/B | 12.1 | 17.6 | 30.1 | 59 | 12 | 85.5 |
| Pool P2/10 | 11.1 | 15.6 | 26 | 51.1 | — | 97.8 |
| Pool P2/20 | 10.8 | 15.2 | 24.5 | 50.2 | 10.8 | 102.5 |

**Calculated with CCN plasma lot 049 Calibration Curve: PT % = 85%, FVII % = 105%

TABLE 15

Pool P2 after the lyophilization

Lyophilized calibrator test with INNOVIN ™ PT Reagent

|  | Calibration Curve | | | | Test | PT % |
|---|---|---|---|---|---|---|
| Calibrator | Neat | 1 in 2 | 1 in 4 | 1 in 8 | Mode | ** |
| Pool P2 | 12.2 | 18.6 | 32.3 | 66.6 | 12.3 | 82.5 |
| Pool P2/B | 12 | 18.6 | 32.1 | 65.1 | 12.3 | 82.5 |
| Pool P2/10 | 11.4 | 16.7 | 29.1 | 60.3 | 11.65 | 89.5 |
| Pool P2/20 | 11.1 | 16.6 | 28.6 | 57.7 | 11.3 | 94.8 |

Frozen calibrator test with INNOVIN ™ PT Reagent

|  | Calibration Curve | | | | Test | PT % |
|---|---|---|---|---|---|---|
| Calibrator | Neat | 1 in 2 | 1 in 4 | 1 in 8 | Mode | ** |
| Pool P2 | 11.7 | 17.4 | 30.2 | 59.3 | 11.65 | 901 |
| Pool P2/B | 11.7 | 17.2 | 30.1 | 59.4 | 11.85 | 87.6 |
| Pool P2/10 | 11 | 15.5 | 26.3 | 52 | 11.1 | 97.8 |
| Pool P2/20 | 10.7 | 15.3 | 25.5 | 51 | 10.5 | 107.7 |

Lyophilized calibrator test with THROMBOPLASTIN IS PT Reagent

|  | Calibration Curve | | | | Test | PT % |
|---|---|---|---|---|---|---|
| Calibrator | Neat | 1 in 2 | 1 in 4 | 1 in 8 | Mode | ** |
| Pool P2 | 15.2 | 20.1 | 34.3 | 66.2 | 15.7 | — |
| Pool P2/B | 14.9 | 22.7 | 37.7 | 73.3 | 15 | — |
| Pool P2/10 | 14.1 | 21.1 | 34.3 | 67.8 | 14.1 | — |
| Pool P2/20 | 13.6 | 20.1 | 34.3 | 66.2 | 13.7 | — |

TABLE 16

Frozen Pool P2
Frozen calibrator test with THROMBOPLASTIN IS PT Reagent

|  | Calibration Curve | | | | Test | PT % |
|---|---|---|---|---|---|---|
| Calibrator | Neat | 1 in 2 | 1 in 4 | 1 in 8 | Mode | ** |
| Pool P2 | 14.7 | 22.6 | 37.5 | 74.3 | 14.95 | — |
| Pool P2/B | 14.9 | 22.5 | 37.3 | 72.6 | 15 | — |
| Pool P2/10 | 13.7 | 20.3 | 33.8 | 67.6 | 13.7 | — |
| Pool P2/20 | 13.1 | 19.5 | 32.9 | 64.6 | 13.1 | — |

**Calculated with CCN plasma lot 049 calibration curve: PT % = 85%, FVII % = 105%

EXAMPLE VII

The accelerated stability of Pool P2 (as prepared in Example VI) with rFVIIa added was tested and compared with two lots of CCN plasma. Reagents used were Pools P2, P2/13, P2/10, P2/20, CNN plasma lots 050 and 053. Several vials of the plasmas were stored at 37° C. and tested after 10, 14, 26 and 35 days on the MLA Electra 1000C according to the Box Insert and the MLA Electra 1000C Handbook. Vials of the same plasmas stored at 4° C. were tested for the same time periods. All plasma tested showed a progressive drop in the PT % on incubation at 37° C. The plasma containing rFVIIa did not drop differently than those not containing rFVIIa. Adding rFVIIa does not change the stability of the plasma incubated at 37° C. measured using the PT % assay. See Table 17. Subsequent analysis of further lots with Arrhenius stability testing has given a predicted shelf life of greater than 2 years.

TABLE 17

Accelerated stability Pool P2

Prothrombin Time in %

| Calibrator | 10 days | | 14 days | | 26 days | | 35 days | |
|---|---|---|---|---|---|---|---|---|
| | 4° C. | 37° C. | 4° C. | 37° C. | 4° C. | 37° C. | 4° C. | 37° C. |
| CCN 050 | 83.6 | 79.4 | 84.7 | 76.5 | 83.6 | 76.5 | 83.6 | 79.7 |
| CCN 053 | 83.6 | 78.4 | 83.6 | 76.5 | 82.5 | 75.7 | 83.6 | 73.0 |
| Pool P2 | 83.6 | 78.4 | 83.6 | 76.5 | 83.6 | 73.8 | 83.6 | 71.3 |
| Pool P2/B | 84.7 | 78.4 | 84.7 | 76.5 | 83.6 | 73.8 | 84.7 | 73.0 |
| Pool P2/10 | 92.1 | 85.8 | 90.8 | 83.6 | 92.1 | 80.4 | 92.1 | 79.4 |
| Pool P2/20 | 94.8 | 89.5 | 96.3 | 85.8 | 94.8 | 83.6 | 96.3 | 81.4 |

PT % is calculated with CCN lot 049 Calibration Curve: PT %=85%.

EXAMPLE VIII

A previously prepared pool of citrated plasma, from 10 donors (See Table 6a), stored at −20° C., was thawed in a 37° C. waterbath and then stored at 4° C. When the temperature of the thawed plasma reached 4° C., then a HEPES solution was added slowly dropwise.

The HEPES solution was prepared by adding 40 mg of HEPES powder to 100 ml distilled water. The pH was adjusted to approximately 7.3 to 7.5 using 5M NaOH. (About 5 ml of 5M NaOH was needed.) This resulted in a 40% HEPES solution (lot H1-83).

For each liter of plasma in the pool, 30 ml of the 40% HEPES solution were added. The pooled plasma and the HEPES solution were mixed for 10 minutes, with care not to create foam.

All testing was performed using an MLA Electra 1000C. The PT % of the pool plus HEPES buffer (the "Buffered Pool") was determined. Recombinant Factor VIIa was then added to the Buffered Pool in a step-wise manner, as described below, until the PT % of the Buffered Pool plus rFVIIa was between 105% and 108%. It was adjusted 5–8% above 100% to allow for PT % loss of 5–8% during lyophilization. The rFVIIa had previously had its activity determined by adding dilutions to plasma (as described in Example IV), and this activity was used in the following formula to determine the amount (in ml) of rFVII to add per ml of Buffered Pool.

Amount rFVIIa (ml) =

$$\frac{\text{(Volume of Buffered Pool (ml)} \times \text{U/ml } rFVII \text{ required)}}{rFVIIa \text{ concentration (U/ml)}}$$

The total amount of rFVIIa that should be added to the Buffered Pool to achieve a PT % of 105–108% is about 0.6 Units per ml of plasma. If the PT % is as follows, then the amount of rFVIIa that is required is as follows:

| | |
|---|---|
| <90% | add 0.6 U/ml |
| <100% | add 0.3 U/ml |
| <105% | add 0.15 U/ml. |

Once the target PT % activity of the plasma pool with rFVIIa was achieved, the mixture was again thoroughly stirred for at least two minutes. Two aliquots of the mixture were tested and the mean of all 8 results was calculated. If the mean result was between 105–108% (inclusive), the material was accepted for lyophilization. If need be, further buffered plasma that has not had rFVIIa added to it can be added to the Buffered Pool to reduce the PT % to achieve the required value. See Tables 18–20. Data from a pilot production size run is shown in Tables 18, 19, and 20.

TABLE 18

Pre-Lyophilization Testing Calibration plasma curve

| | Dilution of Plasma | | | |
|---|---|---|---|---|
| | Neat | 1/2 | 1/4 | 1/8 |
| Sample 1 | 11.8 | 16.8 | 27.9 | 56.7 |
| | 11.8 | 16.6 | 27.7 | 54.5 |
| Sample 2 | 11.5 | 16.7 | 29.8 | 55.7 |
| | 11.3 | 16.2 | 28.3 | 56.5 |
| Sample 3 | 11.4 | 16.3 | 27.2 | 54.6 |
| | 11.3 | 16.1 | 27.7 | 53.9 |
| Mean* | 11.5 | 16.5 | 28.1 | 55.3 |
| PT % | 88 | 44 | 22 | 11 |
| | | | COD | 0.939 |

TABLE 19

Reagents used

| | |
|---|---|
| Calibration Plasma | |
| Lot No. | R&D Pool P3 |
| PT % with INNOVIN | 88 |
| rFVIIa conc. Lot No. | 21593 |
| rFVIIa conc. (U/ml) | 2500 |
| Innovin ™ Lot No. | TFS-12 |
| Saline Lot No. | H1-86 |
| Machine type | 1000C |
| Machine No. | 187 |
| Programme version | 3.E |

Testing of Plasma Pool
Measured volume (ml) 1200

Reserved plasma volumes (ml) 200
Numbers of donor units 10

TABLE 20

Results obtained

| Material Tested | Clotting Time (Secs) | | Calculated PT % | | Mean |
|---|---|---|---|---|---|
| Initial Pool R&D Pool P3 Calibration Plasma | 12.5 | 12.3 | 75.6 | 77.8 | 77.1 |
| | 12.2 | 12.5 | 78.9 | 75.6 | |
| | 12.3 | 12.4 | 77.8 | 76.7 | |
| Plasma Pool plus 0.3 U/ml plasma rFVIIa Volume of rFVIIa added = 0.12 ml | 11.2 | 10.9 | 92.5 | 97.5 | 95.0 |
| | 11.0 | 11.1 | 95.8 | 94.1 | |

Further addition of rFVIIa

| Volume | U/ml Plasma | Plasma (ml) | | | | | |
|---|---|---|---|---|---|---|---|
| 0.06 | 0.15 | 0 | 95.8 | 99.3 | 11.0 | 10.8 | 98.9 |
| | | | 99.3 | 101.2 | 10.8 | 10.7 | |
| 0.06 | 0.15 | 0 | 101.2 | 105.1 | 10.7 | 10.5 | 104.7 |
| | | | 105.1 | 107.2 | 10.5 | 10.4 | |
| 0.03 | 0.075 | 0 | 105.1 | 105.1 | 10.5 | 10.5 | 104.7 |
| | | | 101.2 | 107.2 | 10.7 | 10.4 | |
| 0.03 | 0.075 | 0 | 107.2 | 107.2 | 10.4 | 10.4 | 104.8 |
| | | | 107.2 | 109.4 | 10.4 | 10.3 | |
| 0 | 0 | 0 | 103.2 | 109.4 | 10.6 | 10.3 | 107.3 |
| | | | 107.3 | 109.4 | 10.4 | 10.3 | |

Final PT % 107.3

Testing of the lyophilized product was performed using the MLA Electra 1000C. A lyophilized plasma that had been calibrated against FNP was used as a calibrator ("the Calibrator"). The PT % of the lyophilization product was calculated (using only the results from the undiluted plasma). This was assigned as the PT % of the product. A calibration curve was then obtained using the lyophilized product. As an in-process control check of the lyophilized product, a range of test results (see Tables 21–24) were calculated using the lyophilized product and the Calibrator, and the percentage difference was calculated. The lyophilized product was deemed to be acceptable if there were no differences greater than 15% (See Table 25).

TABLE 21

Post-Lyophilization Testing: Calibration plasma curve

| | Dilution of Plasma | | | |
|---|---|---|---|---|
| | Neat | 1/2 | 1/4 | 1/8 |
| Sample 1 | 11.5 | 16.3 | 27.9 | 53.5 |
| | 11.5 | 16.2 | 26.4 | 53.7 |
| Sample 2 | 11.3 | 16.1 | 27.8 | 53.0 |
| | 11.2 | 16.0 | 26.7 | 54.6 |
| Sample 3 | 11.2 | 16.1 | 27.5 | 52.8 |
| | 11.2 | 16.1 | 26.6 | 53.3 |
| Mean | 11.5 | 16.1 | 27.2 | 53.5 |
| PT % | 86 | 44 | 22 | 11 |
| | | | COD | 0.931 |

TABLE 22

Reagents Used

| Calibration Plasma | |
|---|---|
| Lot No. | R&D Pool P3 |
| PT % with INNOVIN ™ | 88 |
| Innovin ™ Lot No. | TFS-12 |
| Saline Lot No. | H1-86 |
| Machine Type | 1000C |
| Machine No. | 187 |
| Programme version | 3.E |

TABLE 23

INNOVIN PT Calibrator:

| | Dilution of Plasma | | | |
|---|---|---|---|---|
| | Neat | 1/2 | 1/4 | 1/8 |
| Sample 1 | 10.4 | 15.1 | 26.0 | 54.1 |
| | 10.6 | 15.1 | 26.5 | 51.2 |
| Sample 2 | 10.6 | 15.5 | 26.8 | 51.1 |
| | 10.7 | 15.3 | 26.1 | 50.8 |
| Sample 3 | 10.5 | 15.8 | 27.1 | 51.1 |
| | 10.7 | 15.5 | 26.8 | 52.1 |
| Mean | 10.6 | 15.4 | 26.5 | 51.2 |
| PT % | 104 | 52 | 26 | 13 |
| | | | COD | 0.947 |

TABLE 24

Final Results of Pool P4

| IPTC Lot | R&D Pool P4 |
|---|---|
| PT % with INNOVIN ™ | 104 |
| rFVIIa conc Lot No. | 21593 |
| Units added/ml plasma | 0.75 |

TABLE 25

Comparison of calculation with IPTC and CoagCal N:

| Test Results (secs.) | PT % Calculated Using IPTC | PT % Calculated Using CoagCal N | % Difference CCPT/CCN |
|---|---|---|---|
| 9 | 142.5 | 151.0 | 5.6 |
| 9.5 | 127.4 | 131.7 | 3.2 |
| 10 | 115.2 | 116.8 | 1.4 |
| 11 | 96.7 | 95.3 | 1.5 |
| 12 | 83.3 | 80.4 | 3.6 |
| 13 | 73.1 | 69.6 | 5.0 |
| 14 | 65.1 | 61.33 | 6.19 |
| 16 | 53.6 | 49.6 | 8.1 |
| 20 | 39.5 | 35.8 | 10.3 |
| 25 | 29.7 | 26.6 | 11.7 |
| 30 | 23.8 | 21.1 | 12.8 |
| 40 | 17.1 | 15.0 | 14.0 |
| 50 | 13.2 | 11.6 | 13.8 |
| 60 | 10.9 | 9.5 | 14.7 |
| 70 | 9.2 | 8.0 | 15.0 |

Final PT % 104

EXAMPLE IX

The stability of the first Pilot production (identified here as Lot P4), when reconstituted, was tested using Innovin™ reagent lot TFS-12 and Saline H1-86. Dilution stability testing was performed on the MLA Electra 900C using programme version 4.1.

The testing was performed immediately after the dilutions had been prepared (t=0) and exactly 30 minutes after preparation (t=30). All reconstituted stability testing was performed using the E1000C using programme version 3E. Six vials were reconstituted. Three were left at room temperature for 8 hours and three at 4° C. for 8 hours. After 8 hours, three more vials were freshly reconstituted and all nine vials had calibration curves produced. Innovin™ reagent was freshly reconstituted and tested immediately, after 4 and 8 hours stored on the E1000C (8° C.) using freshly reconstituted reagents at each time point.

The material was deemed not to have failed stability testing if the clotting time in seconds was not more than 10% different from the clotting time obtained from lyophilized material stored at 4° C. that had been freshly tested after reconstitution. The plasma dilutions were stable for 30 minutes. See Table 26. There was no significant variation between time 0 and time 30. The stability of INNOVIN™ reagent on the Electra 1000C is also good for 8 hours at 8° C. (Table 27). The results do not give a variation from time t=0 until time t=8 hours. The PT calibrator reconstituted stability was also measured for 8 hours. There is little change between time t=0 and time t=8 hours at either 4° C. (2%) or room temperature (4%). See Table 28.

The testing confirms the stability of the dilutions, the stability of INNOVIN™ TFS-12 and the reconstituted stability of Pilot lot P4.

TABLE 26

Stability of the Dilutions of PT Calibrator:

| | \multicolumn{8}{c}{Incubation Time} | | | | | | | |
|---|---|---|---|---|---|---|---|---|
| | 0 Minutes Dilution of plasma | | | | 30 Minutes Dilution of Plasma | | | |
| | Neat | 1 in 2 | 1 in 4 | 1 in 8 | Neat | 1 in 2 | 1 in 4 | 1 in 8 |
| Sample 1 | 11.1 | 13.5 | 20.0 | 36.0 | 11.1 | 13.1 | 20.9 | 37.0 |
| | 10.9 | 13.0 | 19.2 | 36.6 | 10.8 | 13.0 | 19.3 | 35.9 |
| Sample 2 | 11.4 | 13.0 | 19.4 | 37.9 | 11.0 | 12.7 | 19.7 | 37.4 |
| | 10.7 | 12.6 | 19.6 | 36.0 | 10.5 | 12.7 | 19.8 | 34.8 |
| Sample 3 | 10.7 | 12.5 | 21.0 | 37.5 | 10.9 | 12.8 | 20.0 | 35.0 |
| | 10.4 | 12.5 | 19.1 | 38.4 | 10.4 | 12.9 | 18.9 | 24.5 |
| Mean | 10.87 | 12.85 | 19.72 | 37.07 | 10.78 | 12.87 | 19.77 | 35.77 |

TABLE 27

Stability of INNOVIN ™ Reagent on the Electra 1000C

| | \multicolumn{12}{c}{Incubation Time} | | | | | | | | | | | | |
|---|---|---|---|---|---|---|---|---|---|---|---|---|
| | 0 Hours Dilution of plasma | | | | 4 Hours Dilution of plasma | | | | 8 hours Dilution of plasma | | | |
| Sample | Neat | 1 in 2 | 1 in 4 | 1 in 8 | Neat | 1 in 2 | 1 in 4 | 1 in 8 | Neat | 1 in 2 | 1 in 4 | 1 in 8 |
| 1 | 10.9 | 15.3 | 24.9 | 49.0 | 10.7 | 15.0 | 25.3 | 49.9 | 10.8 | 16.0 | 27.3 | 53.9 |
| | 11.0 | 14.9 | 24.4 | 48.9 | 10.7 | 15.1 | 25.2 | 49.4 | 10.6 | 15.9 | 26.8 | 52.6 |
| 2 | 11.0 | 16.2 | 27.5 | 54.8 | 10.9 | 16.0 | 27.3 | 54.5 | 10.8 | 16.5 | 27.8 | 53.2 |
| | 10.7 | 16.2 | 26.9 | 55.2 | 11.0 | 15.9 | 27.8 | 55.5 | 10.7 | 16.0 | 26.7 | 53.4 |
| 3 | 10.8 | 16.0 | 28.1 | 52.7 | 10.9 | 16.2 | 27.6 | 55.5 | 10.7 | 16.6 | 27.3 | 54.0 |
| | 10.8 | 16.2 | 27.9 | 53.0 | 10.8 | 16.1 | 27.4 | 61.7 | 10.9 | 16.0 | 26.9 | 55.5 |
| Mean | 10.87 | 15.80 | 26.62 | 52.27 | 10.83 | 15.72 | 26.77 | 54.42 | 10.75 | 16.17 | 27.13 | 53.77 |

TABLE 28

PT Calibrator: reconstituted stability of 8 hours
Incubation Time

| | 0 hours Dilution of plasma | | | | 4 hours Dilution of plasma | | | | 8 hours Dilution of plasma | | | |
|---|---|---|---|---|---|---|---|---|---|---|---|---|
| Sample | Neat | 1 in 2 | 1 in 4 | 1 in 8 | Neat | 1 in 2 | 1 in 4 | 1 in 8 | Neat | 1 in 2 | 1 in 4 | 1 in 8 |
| 1 | 10.90 | 15.90 | 26.80 | 54.80 | 11.30 | 17.30 | 28.80 | 56.10 | 10.90 | 15.90 | 27.20 | 56.90 |
| | 10.70 | 16.00 | 27.30 | 56.00 | 11.20 | 16.50 | 28.60 | 55.90 | 10.80 | 15.90 | 27.50 | 52.30 |
| 2 | 10.90 | 15.90 | 28.10 | 54.20 | 11.30 | 16.10 | 28.70 | NCD | 11.10 | 16.10 | 27.80 | 54.40 |
| | 10.70 | 15.80 | 27.80 | 56.10 | 10.90 | 17.30 | 27.80 | 56.80 | 10.90 | 16.50 | 26.60 | 55.40 |
| 3 | 10.70 | 16.60 | 26.60 | NCD | 11.10 | 16.60 | 28.60 | 54.50 | 11.00 | 16.10 | 27.20 | 55.60 |
| | 10.50 | 16.00 | 27.50 | 53.50 | 10.90 | 16.50 | 27.40 | 55.10 | 10.80 | 15.70 | 28.80 | 52.90 |
| Mean | 10.73 | 16.03 | 27.35 | 54.92 | 11.12 | 16.72 | 28.32 | 55.68 | 10.92 | 16.03 | 27.52 | 54.58 |

RT = Room Temperature = 24° C.
NCD = No Clot Detected

EXAMPLE X

Further stability testing was performed on Lot P4. The failure criterion was defined as a change of 10% in the Clotting Time (in seconds) as compared with the mean baseline value.

The accelerated stability calculation with the Arrhenius method was calculated with the SigmaPlot program as follows:

1. For each temperature plot decimal log of concentration (in this case—Clotting Time in seconds) (Y axis) against the time (in this case—days) (X axis) (Table 29).

2. For each temperature (graph) calculate the regression equation Y=m X+b.

3. Define a percent change at which the product is no longer acceptable, (in this case—+10% of Clotting time; mean baseline+10%=10.69+10%=11.76 seconds), convert the value of the zero time analyses to decimal log concentration (in this case—Log of Clotting Time(s)=log of 11.76–1.070).

4. Using the regression equations for each temperature, substitute the decimal log and calculate the day failure.

5. Plot decimal log days from section 4, against 1/absolute temperature (Table 30).

6. Calculate the regression equation Y=m X+b, for the graph in section 5.

7. Using the regression equation from section 6, calculate the expected shelf life at 4° C.

Table 31 shows baseline date which demonstrates the reproducibility between different vials of Lot P4. Tables 32 and 33 show the results of testing of controls during the stability testing. Table 34 shows that the stability of Lot P4 failed after 45 days at room temperature (25° C.). Table 35 shows the stability of Lot P4 at 30° C.; Table 36 shows the stability of Lot P4 at 37° C.; and Table 37 shows the stability of Lot P4 at 50° C.

TABLE 29

Calculation of failure day for each temperature

| Temperature | X axis Days | Clotting time (secs.) | Decimal Log of CT (secs.) | Statistics | Failure Day |
|---|---|---|---|---|---|
| at 25° C. (Room temp.) | 0 | 10.69 | 1.029 | | |
| | 5 | 11.10 | 1.045 | | |
| | 11 | 11.28 | 1.052 | | |
| | 15 | 11.38 | 1.056 | | |
| | 20 | 11.20 | 1.049 | | |
| | 32 | 11.62 | 1.065 | | |
| | 37 | 11.52 | 1.061 | r = 0.933 | |
| | 45 | 11.73 | 1.069 | I = 1.038 | |
| | 56 | 12.00 | 1.079 | s = 0.00072 | 44.4 days |
| at 30° C. | 0 | 10.69 | 1.029 | | |
| | 3 | 11.13 | 1.046 | | |
| | 4 | 11.47 | 1.060 | | |
| | 7 | 11.65 | 1.066 | | |
| | 8 | 11.63 | 1.066 | | |
| | 9 | 11.73 | 1.069 | | |
| | 10 | 11.73 | 1.069 | | |
| | 14 | 12.05 | 1.081 | | |
| | 16 | 12.15 | 1.085 | r = 0.96956 | |
| | 18 | 12.33 | 1.091 | I = 1.039 | |
| | 20 | 12.60 | 1.100 | s = 0.00304 | 10.2 days |

TABLE 29-continued

Calculation of failure day for each temperature

| | | | | | |
|---|---|---|---|---|---|
| at 37° C. | 0 | 10.69 | 1.029 | | |
| | 1 | 11.30 | 1.053 | | |
| | 2 | 11.45 | 1.059 | | |
| | 3 | 11.62 | 1.065 | | |
| | 4 | 11.68 | 1.067 | r = 0.96541 | |
| | 5 | 12.08 | 1.082 | I = 1.037 | |
| | 6 | 12.32 | 1.091 | s = 0.009 | 3.67 days |
| at 50° C. | 0 | 10.69 | 1.029 | | |
| | 0.083 (2 hrs) | 11.12 | 1.046 | | |
| | 0.167 (4 hrs) | 11.32 | 1.054 | r = 0.97223 | |
| | 0.25 (6 hrs) | 11.45 | 1.059 | I = 1.033 | |
| | 0.333 (8 hrs) | 11.67 | 1.067 | s = 0.1068 | 0.346 day |

Formula $Y = 1.070$
$Y = mX + b$   $m$ = slope (s)
$X = Y - b/m$   $b$ = Intercept (I)

TABLE 30

Calculation of shelf life stability at 4° C.

| X-axis | | Y axis | | |
|---|---|---|---|---|
| Temperature | 1/temperature | failure day | log failure day | Statistics |
| 25° C. | 0.04 | 44.4 | 1.65 | |
| 30° C. | 0.033 | 10.2 | 1.0086 | r = 0.953 |
| 37° C. | 0.027 | 3.67 | 0.56 | I = 0.7046 |
| 50° C. | 0.02 | 0.346 (8.1 hours) | −0.46 | s = 18.875 |

Formula $X = 0.25$ (1.4° C.)
$Y = mX + b$   m = Slope (s) = 18.875
   b = Intercept (I) = −0.7046

$Y = 18.875 \times 0.25 + (-0.7046) = 4.014$
=> inv. log of 4.014 = 10327 days stable>
=> 28.3 years
28 years − 33% = 18 years In conclusion, Lot P4 is stable 18 years at 4° C.

TABLE 31

Stability testing - Baseline Data

| Assay: | Prothrombin Time | |
|---|---|---|
| Reagents: | INNOVIN PT Calibrator lot | PILOT LOT 1 (P4) |
| | INNOVIN reagent lot | TFS - 12 |
| | Saline 0.9% Lot | H1 - 86 |
| Machine: | MLA E1000C Software Version | 5.00E P46 |

Clotting Time (Secs.)

| Vials | Reference Tested | Neat | | 1 in 2 | | 1 in 4 | | 1 in 8 | |
|---|---|---|---|---|---|---|---|---|---|
| 1 | FIG. 14 NB CO82 P84 | 10.4 | 10.6 | 15.1 | 15.1 | 26.0 | 26.5 | 54.1 | 51.2 |
| 2 | | 10.6 | 10.7 | 15.5 | 15.3 | 26.8 | 26.1 | 51.1 | 50.8 |
| 3 | | 10.5 | 10.7 | 15.8 | 15.5 | 27.1 | 26.8 | 51.1 | 52.1 |

TABLE 31-continued

Stability testing - Baseline Data

| Assay: | Prothrombin Time | |
|---|---|---|
| Reagents: | INNOVIN PT Calibrator lot | PILOT LOT 1 (P4) |
| | INNOVIN reagent lot | TFS - 12 |
| | Saline 0.9% Lot | H1 - 86 |
| Machine: | MLA E1000C Software Version | 5.00E P46 |

Clotting Time (Secs.)

| | | Neat | | 1 in 2 | | 1 in 4 | | 1 in 8 | |
|---|---|---|---|---|---|---|---|---|---|
| 4 | Table 32 NB Co82 P 84 | 10.6 | 10.4 | 15.4 | 15.4 | 26.8 | 26.2 | 53.0 | 51.6 |
| 5 | | 10.6 | 10.5 | 15.5 | 15.4 | 26.1 | 26.1 | 52.3 | 52.6 |
| 6 | | 10.6 | 10.5 | 15.4 | 15.4 | 26.3 | 25.8 | 53.0 | 51.8 |
| 7 | Table 45 NB Co95 p2 | 10.9 | 11.0 | 15.3 | 14.9 | 24.9 | 24.9 | 49.0 | 48.9 |
| 8 | | 11.0 | 10.7 | 16.2 | 16.2 | 27.5 | 26.9 | 54.8 | 55.2 |
| 9 | | 10.8 | 10.8 | 16.0 | 16.2 | 28.1 | 27.9 | 52.7 | 53.0 |
| 10 | Table 46 NB CO95 p3 | 10.9 | 10.7 | 15.9 | 16.0 | 26.8 | 27.3 | 54.8 | 56.0 |
| 11 | | 10.9 | 10.7 | 15.9 | 15.8 | 28.1 | 27.8 | 54.2 | 56.1 |

| | Mean | 10.69 | 15.60 | 26.67 | 52.70 |
|---|---|---|---|---|---|
| | SD | 0.178 | 0.382 | 0.902 | 1.996 |
| | CV | 1.666 | 2.447 | 3.384 | 3.787 |
| | Mean + 10% | 11.76 | 17.16 | 29.34 | 57.97 |
| | Mean + 10% | 9.62 | 14.04 | 24.00 | 47.43 |

TABLE 32

Stability testing - Controls

Coag Cal N
Lot No: 540.053
Innovin ™ PT % 85

| Assay: | Prothrombin Time | |
|---|---|---|
| Reagents: | INNOVIN ™ lot | TFS-12 |
| | Saline 0.9% lot | H1-86 H1-87 |
| Machine: | MLA E1000C Software version | 5.00 E P 46 |

Clotting Time (Seconds)

| CoagCalN | Neat | 1 in 2 | 1 in 4 | 1 in 8 |
|---|---|---|---|---|
| Sample 1 | 12.1 | 17.5 | 31.2 | 61.7 |
| | 12.1 | 17.5 | 29.5 | 56.1 |
| Sample 2 | 12.2 | 17.6 | 29.9 | 57.7 |
| | 12.0 | 17.9 | 30.0 | 58.6 |
| Sample 3 | 12.1 | 17.6 | 30.0 | 58.4 |
| | 12.0 | 17.7 | 30.1 | 57.6 |
| Mean | 12.08 | 17.63 | 30.12 | 58.35 |
| PT % | 85 | 42.5 | 21.25 | 10.625 |

| Date | Control | Clotting Time (seconds) | | Mean | PT % |
|---|---|---|---|---|---|
| 30.11.93 | CTN | 12.9 | 12.8 | 12.85 | 75.6 |
| | CTP | 21.0 | 20.8 | 20.90 | 36.0 |
| 6.12.93 | CTN | 12.7 | 12.5 | 12.60 | 78.3 |
| | CTP | 20.7 | 21.5 | 21.10 | 35.5 |
| 17.12.93 | CTN | 12.9 | 12.7 | 12.80 | 76.1 |
| | CTP | 20.9 | 20.3 | 20.60 | 36.7 |
| 20.12.93 | CTN | 13.1 | 12.9 | 13.00 | 74.1 |
| | CTP | 21.3 | 21.2 | 21.25 | 35.2 |

TABLE 32-continued

Stability testing - Controls

Coag Cal N
Lot No: 540.053
Innovin ™ PT % 85

| Assay: | Prothrombin Time | |
|---|---|---|
| Reagents: | INNOVIN ™ lot | TFS-12 |
| | Saline 0.9% lot | H1-86 H1-87 |
| Machine: | MLA E1000C Software version | 5.00 E P 46 |

| 21.12.93 | CTN | 12.6 | 12.7 | 12.65 | 77.7 |
|---|---|---|---|---|---|
| | CTP | 20.5 | 20.4 | 20.40 | 37.2 |
| 22.12.93 | CTN | 12.4 | 12.4 | 12.40 | 80.6 |
| | CTP | 20.3 | 20.4 | 20.35 | 37.3 |
| 23.12.93 | CTN | 12.6 | 12.4 | 12.35 | 81.2 |
| | CTP | 21.0 | 20.6 | 20.60 | 36.7 |
| 27.12.93 | CTN | 12.6 | 12.5 | 12.50 | 79.4 |
| | CTP | 21.1 | 20.8 | 20.80 | 36.2 |
| 28.12.93 | CTN | 12.6 | 12.5 | 12.50 | 79.4 |
| | CTP | 20.8 | 20.5 | 20.50 | 37.0 |
| 29.12.93 | CTN | 12.5 | 12.5 | 12.50 | 79.4 |
| | CTP | 20.9 | 20.9 | 20.90 | 36.0 |

| Controls | | Lot No. | Assigned Value |
|---|---|---|---|
| CoagTrol N | CTN | 537.001 | 73–99% |
| CoagTrol P | CTP | 541.034 | 29–39% |

TABLE 33

Stability testing - Controls

CoagCal N
Lot No: 540.053
Innovin ™ PT % 85

| Assay: | Prothrombin Time | |
|---|---|---|
| Reagents: | INNOVIN ™ lot | TFS-12 |
| | Saline 0.9% lot | H1-86 H1-87 |
| Machine: | MLA E100C Software version | 5.00 E P 46 |

Clotting Time (Seconds)

| CoagCalN | Neat | 1 in 2 | 1 in 4 | 1 in 8 |
|---|---|---|---|---|
| Sample 1 | 12.1 | 17.5 | 31.2 | 61.7 |
| | 12.1 | 17.5 | 29.5 | 56.1 |
| Sample 2 | 12.2 | 17.6 | 29.9 | 57.7 |
| | 12.0 | 17.9 | 30.0 | 58.6 |
| Sample 3 | 12.1 | 17.6 | 30.0 | 58.4 |
| | 12.0 | 17.7 | 30.1 | 57.6 |
| Mean | 12.08 | 17.63 | 30.12 | 58.35 |
| PT % | 85 | 42.5 | 21.25 | 10.625 |

| Date | Control | Clotting Time(s) | | Mean | PT % |
|---|---|---|---|---|---|
| 30.12 | CTN | 12.5 | 12.3 | 12.40 | 80.6 |
| | CTP | 20.4 | 21.1 | 20.75 | 36.4 |
| 3.01.94 | CTN | 12.6 | 12.6 | 12.60 | 78.3 |
| | CTP | 21.3 | 22.3 | 21.80 | 34.0 |
| 5.01.94 | CTN | 12.6 | 12.5 | 12.55 | 78.8 |
| | CTP | 20.6 | 20.1 | 20.35 | 37.3 |
| 6.01.94 | CTN | 12.7 | 12.5 | 12.60 | 78.3 |
| | CTP | 20.7 | 21.1 | 20.90 | 36.0 |
| 06.01.94 | CTN | 12.5 | 12.5 | 12.50 | 79.4 |
| MLA 900 | CTP | 20.0 | 20.1 | 20.05 | 38.0 |
| 7.01.94 | CTN | 12.7 | 12.5 | 12.60 | 78.3 |
| | CTP | 21.0 | 20.9 | 20.95 | 36.0 |
| 10.01.94 | CTN | 12.6 | 12.6 | 12.60 | 78.3 |
| | CTP | 20.9 | 20.8 | 20.85 | 36.0 |

| Controls | | Lot No. | Assigned Value |
|---|---|---|---|
| CoagTrol N | CTN | 537.001 | 73–99% |
| CoagTrol P | CTP | 541.034 | 29–39% |

TABLE 34

Accelerated Stability

Assay: Prothrombin Time  
Reagents: INNOVIN ™ PT Calibrator lot    PILOT LOT 1  
           INNOVIN ™ lot    TFS-12  
           Saline 0.9% lot    H1-86 H1-87  
           MLA E1000C Software version    5.00E P46  
TEMPERATURE INCUBATED: 20° C.

Mean baseline clotting time (secs)    10.69    PT %    100

Clotting Time of neat plasma (seconds)

| Number of Day | Vial 1 | Vial 2 | Vial 3 | Mean | % Change from Mean | PT % |
|---|---|---|---|---|---|---|
| 5 | 11.2 | 11.3 | 11.3 | 11.10 | 3.84 | 92.8 |
|   | 10.9 | 10.9 | 11.0 |       |      |      |
| 11 | 11.4 | 11.5 | 11.3 | 11.28 | 5.52 | 90.3 |
|    | 11.3 | 11.1 | 11.1 |       |      |      |
| 15 | 11.5 | 11.6 | 11.5 | 11.38 | 6.45 | 88.9 |
|    | 11.3 | 11.2 | 11.2 |       |      |      |
| 20 | 11.3 | 11.2 | —   | 11.20 | 4.77 | 91.4 |
|    | 11.2 | 11.1 | —   |       |      |      |
| 32 | 11.5 | 11.9 | 11.7 | 11.62 | 8.70 | 85.8 |
|    | 11.5 | 11.5 | 11.6 |       |      |      |
| 37 | 11.7 | 11.7 | 11.6 | 11.52 | 7.76 | 87.1 |
|    | 11.4 | 11.4 | 11.3 |       |      |      |
| 45 | 11.9 | 11.8 | 11.9 | 11.73 | 9.73 | 84.5 |
|    | 11.7 | 11.5 | 11.6 |       |      |      |
| 56 | 12.1 | —   | —   | 12.00 | 12.25 | 81.3 |
|    | 11.9 | —   | —   |       |       |      |

Failed stability after (days)    45

TABLE 35

Accelerated Stability

Assay: Prothrombin Time  
Reagents: INNOVIN ™ PT Calibrator lot    PILOT LOT 1  
           INNOVIN ™ lot    TFS-12  
           Saline 0.9% lot    H1-86 H1-87  
           MLA E1000C Software version    5.00E P46  
TEMPERATURE INCUBATED: 30° C.

Mean baseline clotting time (secs)    10.69    PT %    100

Clotting Time of neat plasma (seconds)

| Number of Day | Vial 1 | Vial 2 | Vial 3 | Mean | % Change from Mean | PT % |
|---|---|---|---|---|---|---|
| 3 | 11.3 | 11.3 | 11.3 | 11.13 | 4.12 | 92.4 |
|   | 10.9 | 11.0 | 11.0 |       |      |      |
| 4 | 11.7 | 11.6 | 11.5 | 11.47 | 7.30 | 87.7 |
|   | 11.5 | 11.2 | 11.3 |       |      |      |
| 7 | 11.8 | 11.9 | 11.7 | 11.65 | 8.98 | 85.4 |
|   | 11.5 | 11.5 | 11.5 |       |      |      |
| 8 | 11.7 | 11.7 | 11.7 | 11.63 | 8.79 | 85.7 |
|   | 11.7 | 11.5 | 11.5 |       |      |      |
| 9 | 11.9 | 11.9 | 11.8 | 11.73 | 9.73 | 84.5 |
|   | 11.8 | 11.6 | 11.4 |       |      |      |
| 10 | 11.9 | 11.9 | 11.8 | 11.73 | 9.73 | 84.5 |
|    | 11.6 | 11.8 | 11.4 |       |      |      |
| 14 | 12.1 | 12.2 | 12.1 | 12.05 | 12.72 | 80.8 |
|    | 12.0 | 12.0 | 11.9 |       |       |      |
| 15 | 12.6 | 12.8 | —   | 12.65 | 18.33 | 74.6 |
|    | 12.5 | 12.7 | —   |       |       |      |
| 16 | 12.2 | 12.2 | 12.4 | 12.15 | 13.66 | 79.7 |
|    | 12.0 | 12.1 | 12.0 |       |       |      |
| 18 | 12.5 | 12.4 | 12.3 | 12.33 | 15.34 | 77.8 |
|    | 12.3 | 12.3 | 12.2 |       |       |      |
| 20 | 12.6 | 12.8 | —   | 12.60 | 17.87 | 75.1 |
|    | 12.5 | 12.5 | —   |       |       |      |

Failed stability after (days)    10

TABLE 36

Accelerated Stability

Assay: Prothrombin Time  
Reagents: INNOVIN ™ PT Calibrator lot    PILOT LOT 1  
           INNOVIN ™ lot    TFS-12  
           Saline 0.9% lot    H1-86 H1-87  
           MLA E1000C Software version    5.00E P46  
TEMPERATURE INCUBATED: 37° C.

Mean baseline clotting time (secs)    10.69    PT %    100

Clotting Time of neat plasma (seconds)

| Number of Day | Vial 1 | Vial 2 | Vial 3 | Mean | % Change from Mean | PT % |
|---|---|---|---|---|---|---|
| 1 | 11.4 | 11.5 | 11.3 | 11.30 | 5.70 | 90.0 |
|   | 11.2 | 11.2 | 11.2 |       |      |      |
| 2 | 11.6 | 11.6 | 11.6 | 11.45 | 7.11 | 88.0 |
|   | 11.3 | 11.3 | 11.3 |       |      |      |
| 3 | 11.6 | 11.8 | 11.7 | 11.62 | 8.70 | 85.8 |
|   | 11.6 | 11.5 | 11.5 |       |      |      |
| 4 | 11.8 | 11.9 | 11.9 | 11.68 | 9.26 | 85.1 |
|   | 11.7 | 11.7 | 11.6 |       |      |      |
| 5 | 12.1 | 12.3 | 12.2 | 12.08 | 13.00 | 80.4 |
|   | 12.0 | 12.0 | 11.9 |       |       |      |
| 6 | 12.6 | 12.3 | 12.5 | 12.32 | 15.25 | 77.9 |
|   | 12.2 | 12.0 | 12.3 |       |       |      |

Failed stability after (days)    4

TABLE 37

Accelerated Stability

Assay: Prothrombin Time  
Reagents: INNOVIN ™ PT Calibrator lot    PILOT LOT 1  
           INNOVIN ™ lot    TFS-12  
           Saline 0.9% lot    H1-86 H1-87  
           MLA E1000C Software version    5.00E P46  
TEMPERATURE INCUBATED: 50° C.

Mean baseline clotting time (secs)    10.69    PT %    100

Clotting Time of neat plasma (seconds)

| Number of Day | Vial 1 | Vial 2 | Vial 3 | Mean | % Change from Mean | PT % |
|---|---|---|---|---|---|---|
| 2 | 11.3 | 11.2 | 11.3 | 11.12 | 4.02 | 92.6 |
|   | 11.1 | 11.0 | 10.9 |       |      |      |

TABLE 37-continued

Accelerated Stability

Assay: Prothrombin Time
Reagents: INNOVIN ™ PT Calibrator lot   PILOT LOT 1
          INNOVIN ™ lot                  TFS-12
          Saline 0.9% lot                H1-86 H1-87
          MLA E1000C Software version    5.00E P46
TEMPERATURE INCUBATED: 50° C.

| | | | | | |
|---|---|---|---|---|---|
| 4 | 11.5 | 11.6 | 11.4 | 11.32 | 5.89 | 89.7 |
|   | 11.2 | 11.1 | 11.1 |       |      |      |
| 6 | 11.6 | 11.6 | 11.7 | 11.45 | 7.11 | 88.0 |
|   | 11.2 | 11.2 | 11.4 |       |      |      |
| 8 | 11.7 | 11.7 | 11.8 | 11.67 | 9.17 | 85.2 |
|   | 11.6 | 11.5 | 11.7 |       |      |      |

Failed stability after (hours)   8

We claim:

1. A composition for calibration for a prothrombin time assay comprising:
   a) normal pool plasma selected from the group consisting of citrated plasma and citrate based anticoagulated plasma;
   b) a quantity of a coagulation factor selected from the group consisting of rFVII, rFVIIa, sufficiently purified FVII, and sufficiently purified FVIIa, which when added to said plasma, is sufficient to increase the % PT value of the plasma to about 100% after lyophilization of said normal pool plasma and added coagulation factor.

2. The composition of claim 1 for use with a PT reagent.

3. The composition of claim 1 for use with a recombinant tissue factor reagent.

4. The composition of claim 3 wherein the recombinant tissue factor PT reagent is selected from the group consisting of INNOVIN™ PT reagent and Ortho® RECOMBOPLAS-TIN™ PT reagent.

5. A method of preparing a composition for calibration for use in the prothrombin time assay comprising the steps of:
   a) collecting a normal pool of plasma selected from the group consisting of citrated plasma and citrate based anticoagulant plasma;
   b) adding a quantity of a coagulation factor selected from the group consisting of rFVII, rFVIIa, sufficiently purified FVII, and sufficiently purified FVIIa to said plasma, which is sufficient to increase the % PT of said plasma and added coagulation factor to about 100% PT after lyophilization.

6. The method of claim 5 wherein the composition is used with INNOVIN™ PT reagent.

7. The method of claim 5 wherein the calibrator is used with a recombinant tissue factor PT reagent.

8. The method of claim 7 wherein the recombinant PT reagent is selected from the group consisting of INNOVIN™ PT reagent and Ortho® RECOMBOPLAS-TIN™ reagent.

9. A composition for calibration for a coagulation factor assay comprising:
   a) normal pool plasma selected from the group consisting of citrated plasma and citrate based anticoagulant plasma;
   b) a quantity of coagulation factor selected from the group consisting of rFVII, rFVIIa, sufficiently purified FVII, and sufficiently purified FVIIa which when added to said plasma, is sufficient to increase the percentage of said coagulation factor of the plasma to about 100% after lyophilization of said normal pool plasma and added coagulation factor.

10. A method of preparing a composition for calibration for use in a coagulation factor assay comprising the steps of:
    a) collecting a normal pool plasma selected from the group consisting of citrated plasma and citrate based anticoagulant plasma;
    b) adding a quantity of coagulation factor selected from the group consisting of rFVII, rFVIIa, sufficiently purified FVII, and sufficiently purified FVIIa which when added to said plasma, is sufficient to increase the percentage of said coagulation factor of the plasma to about 100% after lyophilization of said normal pool plasma and added coagulation factor.

* * * * *

UNITED STATES PATENT AND TRADEMARK OFFICE
CERTIFICATE OF CORRECTION

PATENT NO. : 5,866,425
DATED : February 2, 1999
INVENTOR(S) : Barry J. Woodhams, et al.

It is certified that error appears in the above-identified patent and that said Letters Patent is hereby corrected as shown below:

Column 2,
Line 52, delete "acetone dehydrated" and insert -- acetone-dehydrated --.
Line 55, delete "rain" and insert -- brain --.
Line 55, delete "thromboplasint" and insert -- thromboplastin --.
Line 59, delete "antimicrobial" and insert -- Antimicrobial --.
Line 64, delete "Reagent" and insert -- reagent --.
Line 67, after "RECOMBOPLASTIN™" insert -- mixture of highly purified phospholipds and human recombinant tissue factor combined in standarized liposomes, calcium chloride, buffer, and sodium azide as preseravtive, hereinafter RECOMBOPLASTIN reagent --

Column 3,
Line 28, delete "calibrator" and insert -- Calibrator --.

Column 4,
Line 14, delete "calibrator" and insert -- Calibrator --.

Column 5,
Line 50, delete "calibrator" and insert -- Calibrator --

UNITED STATES PATENT AND TRADEMARK OFFICE
CERTIFICATE OF CORRECTION

PATENT NO. : 5,866,425
DATED : February 2, 1999
INVENTOR(S) : Barry J. Woodhams, et al.

It is certified that error appears in the above-identified patent and that said Letters Patent is hereby corrected as shown below:

Column 10,
Line 40, delete "calibrator" and insert -- Calibrator --.

Column 13,
Line 21, delete "calibrator" and insert -- Calibrator --.
Line 58, delete "Table 1ib:" and insert -- Table 11b --.

Column 17,
Line 39, delete "calibrator" and insert --Calibrator --.

Column 28,
Line 9, delete "calibrator" and insert -- composition --.

Signed and Sealed this

Seventh Day of August, 2001

*Attest:*

NICHOLAS P. GODICI
*Attesting Officer*     *Acting Director of the United States Patent and Trademark Office*